United States Patent [19]

Friedman

[11] 4,001,230

[45] Jan. 4, 1977

[54] 3-(5-NITROIMIDAZOL-2-YL)PYRAZOLO[3,4-d]PYRIMIDINE COMPOUNDS

[75] Inventor: Henry Friedman, Indianapolis, Ind.

[73] Assignee: Eli Lilly and Company, Indianapolis, Ind.

[22] Filed: Jan. 31, 1975

[21] Appl. No.: 545,852

Related U.S. Application Data

[63] Continuation-in-part of Ser. No. 469,256, May 13, 1974, abandoned.

[52] U.S. Cl. .............. 260/247.5 DP; 260/247.1 E; 260/247.2 A; 260/256.4 F; 260/256.5 R; 260/309; 260/310 R; 424/251; 424/248.56; 424/248.54

[51] Int. Cl.² ...................................... C07D 487/04

[58] Field of Search ...... 260/247.2, 247.5, 256.4 F, 260/247.2 A, 247.5 DP, 247.1 E, 256.5 R

[56] References Cited

UNITED STATES PATENTS

| | | | |
|---|---|---|---|
| 3,522,256 | 7/1970 | Berger et al. | 260/250 AC |
| 3,755,324 | 8/1973 | Hoyle et al. | 260/256.4 F |

FOREIGN PATENTS OR APPLICATIONS

| | | | |
|---|---|---|---|
| 2,218,717 | 11/1972 | Germany | 260/256.4 |
| 7,300,938 | 10/1973 | Netherlands | 260/250 |

Primary Examiner—Henry R. Jiles
Assistant Examiner—R. W. Ramsuer
Attorney, Agent, or Firm—Dwight E. Morrison; Everet F. Smith

[57] ABSTRACT

There are disclosed novel 3-(5-nitroimidazol-2-yl)-pyrazolo[3,4-d]pyrimidine compounds exhibiting utility as antibacterial and antiprotozoal agents.

13 Claims, No Drawings

3-(5-NITROIMIDAZOL-2-YL)PYRAZOLO[3,4-d]PYRIMIDINE COMPOUNDS

CROSS REFERENCE

This application is a continuation-in-part of my copending application Ser. No. 469,256, filed May 13, 1974 now abandoned.

BACKGROUND OF THE INVENTION

1. Field of the Invention

A great deal of research has been conducted to develop agents for the control of bacteria and protozoa. Thus, compounds and methods for controlling *Escherichia coli, Pasteurella multocida, Salmonella typhimurium, T. vaginalis,* and like organisms have been the subject of extended research.

2. Description of the Prior Art

In the prior art, British Pat. No. 1,326,360, published Aug. 8, 1973, teaches 5-nitro-furyl-substituted pyrazole-pyrimidinones, methods for preparing the compounds, and medicaments containing them as the active ingredient. The compounds are taught as possessing activity as antibacterials, anthelmintics, antiprotozoals, coccidiostats, antimalarials, trypanocides, and antimycoplasma agents.

Also in the prior art in U.S. Pat. No. 3,711,495 Jan. 16, 1973), which teaches isoxazalin-3-yl-substituted-5-nitroimidazoles and methods for their preparation. The compounds are taught as being active as trichomonacides and antitrypanosomiasis agents.

In addition, there is in the prior art German Pat. No. 2,218,717, also identified by Derwent No. 74757T, which patent teaches substituted 5-nitrofuryl derivatives of aminopyrazolopyrimidines and methods for their preparation. The compounds are taught as possessing coccidiostatic, trypanocidal, antibacterial, antimycotic, antimycoplasmic, anthelimintic, antiprotozoal, and antimalarial activity, with broad spectrum and very low toxicity. The compounds included are exemplified by 4-amino-1-methyl-3-(5-nitro-2-furyl)-1H-pyrazolo[3,4-d]pyrimidine.

Another prior art reference is U.S. Pat. No. 3,772,294 (Nov. 13, 1973), which is directed to a process for preparing 4-mono-substituted or 4,6-disubstituted-1-pyrazolo[3,4-d]pyrimidines. These compounds are taught as being useful in the treatment of gout.

A further prior art reference is U.S. Pat. No. 3,755,324 (Aug. 28, 1973), which is directed to compounds of the class 3-(5-nitro-2-furyl)-1H-pyrazolo[3,4-d]pyrimidin-4(5H)-one, alleged to have antimicrobial properties and to be useful for treating urinary tract infections in mammals.

Yet another prior art reference is British Pat. No. 1,353,892, published May 22, 1974, directed to nitroimidazolyl-triazolopyridazines, alleged to be active as antimicrobial agents both in vitro and in vivo, particularly against *Trichomonades* and *Salmonella*.

The compounds described in the prior art set forth above differ significantly structurewise from those of the instant application.

SUMMARY OF THE INVENTION

This invention relates to novel 3-(5-nitroimidazol-2-yl)pyrazolo[3,4-d]pyrimidines which are active as antibacterial and antiprotozoal agents, and to methods for the preparation of the compounds. The novel compounds are active against several organisms, including *Escherichia coli, Pasteurella multocida, Salmonella typhimurium, Mycoplasma hyopneumoniae, Mycoplasma synoviae, Treponema hyodysenteriae,* and *Trichomonas vaginalis.*

DESCRIPTION OF THE PREFERRED EMBODIMENT

This invention relates to novel substituted pyrazolopyrimidine compounds. More particularly, it relates to novel 3-(5-nitroimidazol-2-yl)pyrazolo[3,4-d]pyrimidines of the formula wherein
Z is selected from the group consisting of $$-NH-\underset{R^1}{\underset{|}{C}}-NH-\underset{}{\overset{O}{\underset{\|}{C}}}-, \quad -N=\underset{R^3}{\underset{|}{C}}-\underset{R^4}{\underset{|}{N}}-\underset{}{\overset{R^5}{\underset{\|}{C}}}-, \text{ and}$$

$$-N=\underset{H}{\underset{|}{C}}-N=\underset{R^6}{\underset{|}{C}}-;$$

R is $C_1$–$C_3$ alkyl, hydroxy($C_1$–$C_3$) alkyl, or halo($C_1$–$C_3$)alkyl;
$R^1$ is —$CH_2X$;
$R^2$ is $$R^2 \text{ is } -O-\overset{O}{\underset{\|}{C}}-CH_2X;$$

X is bromine, chlorine, fluorine, or iodine;
$R^3$ is hydrogen, $C_1$–$C_4$ alkyl, or $CF_3$;
$R^4$ is hydrogen, $C_1$–$C_4$ alkyl, $(CH_2)_nN(C_1$–$C_4$ alkyl$)_2$, $CH_2CH[O(C_1$–$C_4$ alkyl$)]_2$, $(CH_2)$n-OH, 9-octadecenyl, $R^5$ is NH or oxygen;
$R^6$ is $NH_2$, $NHCOCH_3$, $$\underset{|}{\overset{R^7}{\underset{}{}}}$$
NHCHCO$_2$H, or $NHNH_2$;
$R^7$ is hydrogen or —$CH_2CH_2SCH_3$;
n is 1, 2, 3, or 4;
and the nontoxic, pharmacologically-acceptable salts thereof.

The preferred compounds of this invention include compounds of the generic formula above wherein $$Z \text{ is } -N=\underset{R_3}{\underset{|}{C}}-\underset{R_4}{\underset{|}{N}}-\underset{R_5}{\overset{}{\underset{\|}{C}}}-OR-N=\underset{H}{\underset{|}{C}}-N=\underset{R_6}{\underset{|}{C}}-;$$

R is $C_1$–$C_3$ alkyl, hydroxy($C_1$–$C_3$)alkyl, or halo($C_1$–$C_3$)alkyl;

$R^3$ is hydrogen, $C_1$–$C_4$ alkyl, or $CF_3$;

$R^4$ is hydrogen, $C_1$–$C_4$ alkyl, $(CH_2)_n$—$N(C_1$–$C_4$ alkyl$)_2$,

$R^5$ is NH or oxygen;
$R^6$ is $NH_2$ or $NHNH_2$;
n is 1, 2, 3, or 4; and
the nontoxic, pharmacologically-acceptable salts thereof.

The most preferred compounds of the instant invention include those wherein

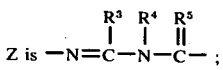

R is $C_1$–$C_3$ alkyl, hydroxy($C_1$–$C_3$)alkyl, or halo($C_1$–$C_3$)alkyl;

$R^3$ is hydrogen;

$R^4$ is hydrogen, $C_1$–$C_4$ alkyl,

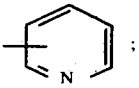

$R^5$ is NH or oxygen;
n is 1, 2, 3, or 4;
and the nontoxic, pharmacologically-acceptable salts thereof.

In the above formula, $C_1$–$C_3$ alkyl represents a straight or branched chain saturated hydrocarbon radical such as methyl, ethyl, n-propyl, or isopropyl.

In the above formula, $C_1$–$C_4$ alkyl represents a straight or branched chain saturated hydrocarbon radical such as methyl, ethyl, n-propyl, isopropyl, n-butyl, sec.-butyl, isobutyl, or t-butyl.

Hydroxy($C_1$–$C_3$)alkyl is hydroxymethyl, hydroxyethyl, or hydroxypropyl.

Halo($C_1$–$C_3$)alkyl is halomethyl, haloethyl, or halopropyl. Halo is bromine, chlorine, fluorine, or iodine.

The novel compounds coming within the scope of the generic formula supra have demonstrated in vitro activity against the following group of microorganisms, many of which are important animal pathogens:

Pseudomonas
*Escherichia coli*
Salmonella
*Pasteurella multocida*
  (cattle)
  (turkey)
Bordetella
Streptococcus
Staphylococcus
*Mycoplasma hyorhinis*
*Mycoplasma synoviae*
*Mycoplasma hyosynoviae*
*Mycoplasma gallisepticum*
*Vibrio coli*
*Mycoplasma hyopneumoniae*
*Klebsiella pneumoniae*
*Aerobacter aerogenes*
*Erwinia amylovora*
*Proteus morganii*
*Trichomonas vaginalis*
*Treponema hyodrysenteriae*

The novel compounds coming within the scope of the generic formula, supra, are readily synthesized utilizing 5-amino-1-methyl3-(1-methyl-5-nitro-2-imidazolyl)-pyrazole-4-carbonitrile.

Thus, the synthesis of certain of the novel compounds of the generic formula, for instance those where

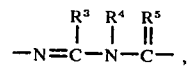

wherein $R^3$= $R^4$= hydrogen, and $R^5$= oxygen, is carried out by heating, that is, refluxing, a mixture of 5-amino-1-methyl-3-(1-methyl-5-nitro-2-imidazolyl)pyrazole-4-carbonitrile and a suitable organic acid, such as formic acid, for a period of time sufficient to complete the reaction. This period of time varies from about 2 hours to about 24 hours. After refluxing for the requisite period of time, the reaction product mixture is cooled and the solvent removed in vacuo to leave a residue. The residue is recrystallized from a suitable solvent to yield the desired product. Suitable solvents for recrystallization include dimethylformamide, commercial absolute ethanol, and the like.

This general procedure is more specifically exemplified as follows.

A mixture of 5-amino-1-methyl-3-(1-methyl-5-nitro-2-imidazolyl)pyrazole-4-carbonitrile and formic acid, suitably 90% formic acid, is heated to refluxing and refluxed for about 2 hours. The reaction product mixture is cooled, and the solvent removed in vacuo, to leave a residue. The residue is recrystallized from a suitable solvent, in this instance, dimethylformamide, to yield a product having a melting point of about 291°–292° C., and identified by elemental analyses and NMR spectrum as 1-methyl-3-(1-methyl-5-nitroimidazol-2-yl)-1H-pyrazolo[3,4-d]pyrimidin-4(5H)-one.

The synthesis of other of the novel compounds, for instance, where Z in the generic formula is

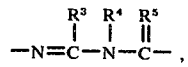

wherein $R^3$ is other than hydrogen, $R^4$ is hydrogen, and $R^5$ is oxygen, is accomplished by heating and refluxing a mixture of the intermediate 5-amino-1-methyl-3-(1-methyl-5-nitro-2-imidazolyl)-pyrazole-4-carbonitrile with a suitable organic acid anhydride, such as propionic anhydride or trifluoroacetic anhydride.

Thus, for example, a mixture of propionic anhydride and 5-amino-1-methyl-3-(1-methyl-5-nitro-2-imidazolyl)pyrazole-4-carbonitrile is refluxed, that is, heated at the refluxing temperature of the reaction mixture, for about 24 hours. The reaction product mixture is allowed to cool to ambient room temperature and the crystals which form are filtered off. The crystals are recrystallized from a suitable solvent, in this case commercial absolute ethanol, to yield product having a melting point of about 243°–245° C., and identified by elemental analyses as 6-ethyl-1,5-dihydro-1-methyl-3-(1-methyl-5-nitro-imidazol-2-yl)-4H-pyrazolo[3,4-d]pyrimidin-4-one.

The novel compound where Z in the generic formula is

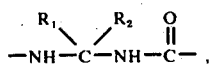

$R_1$ being —$CH_2Cl$, and $R_2$ being

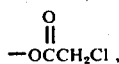

is obtained when a procedure somewhat similar to that just described is followed. In this preparation, 5-amino-1-methyl-3-(1-methyl-5-nitro-2-imidazolyl)pyrazole-4-carbonitrile is refluxed (boiled) with chloroacetic anhydride in the presence of a few drops of concentrated sulfuric acid in a suitable solvent, such as benzene, for about 24 hours. The reaction product mixture is then cooled and filtered. The crude solid thus obtained is recrystallized from a suitable solvent, such as commercial absolute alcohol, to yield product having a melting point of about 217°–218° C. dec. The product is identified by elemental analyses and NMR spectrum as 6-(chloromethyl)-6,7-dihydro-6-hydroxy-1-methyl-3-(1-methyl-5-nitroimidazol-2-yl)-1H-pyrazolo[3,4-d]pyrimidin-4(5H)-one, chloroacetate ester. In this case, the sulfuric acid acts to catalyze the reaction between the acid anhydride and the amino pyrazole carbonitrile to yield the ester.

Still others of the novel compounds of this invention, in particular those where Z in the generic formula is

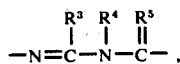

wherein $R^3$ is hydrogen, $R^4$ is other than hydrogen, and $R^5$ is NH, are synthesized by allowing the intermediate compound identified as methyl N-[4-cyano-1-methyl-3-(1-methyl-5-nitro-2-imidazolyl)pyrazol-5-yl]formimidate (such intermediate being prepared as described farther on in this specification) to react with an organic primary amine in a suitable solvent such as ethanol for a period of time sufficient to bring about completion of the reaction. Suitable primary organic amines include ethylamine, n-propylamine, unsym. dimethylethylenediamine, unsym. dimethylpropylenediamine, unsym. diethylethylenediamine, 4-pyridylmethylamine, N-(2-aminoethyl)morpholine, and the like. The time of reaction varies from about 10 minutes to about 24 hours, depending on the nature and identity of the reactants. The reaction temperature varies from ambient room temperature to the refluxing temperature, that is, boiling temperature of the reaction mixture. At the end of the reaction period, the reaction product mixture is cooled and filtered, and the solid which is obtained is recrystallized from a suitable solvent, such as dimethylformamide. This synthesis is illustrated as follows.

A mixture of methyl N-[4-cyano-1-methyl-3-(1-methyl-5-nitro-2-imidazolyl)pyrazol-5-yl]formimidate, n-propylamine, and ethanol is stirred at ambient room temperature for about 10 minutes. The reaction product mixture is filtered and the solid which is obtained is recrystallized from a suitable solvent, such as dimethylformamide. The product obtained has a melting point of about 239°–240° C., and is identified by elemental analyses and NMR spectrum as 4,5-dihydro-4-imino-1-methyl-3-(1-methyl-5-nitroimidazol-2-yl)-5-propyl-1H-pyrazolo-[3,4-d]pyrimidine.

The synthesis of the novel compounds where Z in the generic formula is

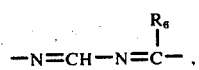

$R^6$ being amino or hydrazino, is accomplished in general by allowing the intermediate compound, identified as methyl N-[4-cyano-1-methyl-3-(1-methyl-5-nitro-2-imidazolyl)pyrazol-5-yl]formimidate, to react with concentrated ammonium hydroxide or with hydrazine, respectively, in a solvent such as ethanol, at the reflux temperature of the mixture, for about an hour. The reaction product mixture is then filtered and the solid product purified by recrystallization. This preparation is illustrated as follows, where $R^6$ in the product is amino.

A mixture of methyl N-[4-cyano-1-methyl-3-(1-methyl-5-nitro-2-imidazolyl)pyrazol-5yl]formimidate and concentrated ammonium hydroxide in commercial absolute ethanol is heated at reflux under a reflux condenser, for about 1 hour. The reaction product mixture is filtered and the solid material which is obtained is recrystallized from a suitable solvent, in this case, dimethylformamide. The product obtained has a melting point of about 317°–318° C. (dec.), and is identified by elemental analyses, and infrared and NMR spectra as 4-amino-1-methyl-3-(1-methyl-5-nitroimidazol-2-yl)-1H-pyrazolo[3,4-d]pyrimidine.

The acetyl derivative of the above compound is readily prepared by allowing a mixture of the 4-amino-1-methyl-3-(1-methyl-5-nitroimidazol-2-yl)-1H-pyrazolo[3,4-d]pyrimidine and acetic anhydride to reflux for about 22 hours. The reaction mixture is cooled and filtered. The solid thus obtained is recrystallized from a suitable solvent such as dimethylformamide to yield crystalline product having a melting point of about 284°–286° C., which product is identified by elemental analyses and NMR spectrum as N-[1-methyl-3-(1-methyl-5-nitroimidazol-2-yl)-1H-pyrazolo[3,4-d]pyrimidin-4-yl]-acetamide.

The novel compound where Z in the generic formula is

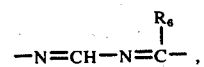

and $R^6$ is —$NHCH_2COOH$, is prepared by heating a mixture of methyl N-[4-cyano-1-methyl-3-(1-methyl-5-nitro-2-imidazolyl)pyrazol-5-yl]formimidate, glycine, and sodium carbonate, in a solvent of equal volumes of ethanol and water to refluxing, and refluxing the mixture for about one and one-half hours. The reaction product mixture is then cooled and filtered. The solid material thus obtained is purified by dissolving in hot water, then cooling and acidifying, using a strong acid such as concentrated sulfuric, concentrated hydrochloric, concentrated hydrobromic, or concentrated phosphoric acid. The acidification causes precipitation of a blue-gray solid. The blue-gray solid is filtered off and recrystallized from dimethylformamide to yield a product having a melting point of about 240°–241° C. The product is identified by elemental analyses and NMR spectrum as N-[1-methyl-3-(1-methyl-5-nitroimidazol-2-yl)-1H-pyrazolo[3,4-d]pyrimidin-4-yl]glycine.

The novel compound where Z in the generic formula is

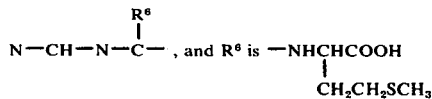

is prepared by heating a mixture of methyl N-[4-cyano-1-methyl-3-(1-methyl-5-nitro-2-imidazolyl)pyrazol-5-yl]formimidate and methionine, following the same general procedure as described above for glycine. The product, having a melting point of about 207°–208° C. (dec.), is identified by elemental analyses, and NMR spectrum as N-[1-methyl-3-(1-methyl-5-nitroimidazol-2-yl)-1H-pyrazolo[3,4-d]-pyrimidin-4-yl]methionine.

In the case of the novel compound where Z in the generic formula is

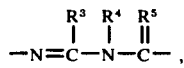

wherein $R^3$=H, $R^4$=CH$_2$CH(OC$_2$H$_5$)$_2$, and $R^5$=NH, the preparation is carried out by stirring a mixture of methyl N-[4-cyano-1-methyl-3-(1-methyl-5-nitro-2-imidazolyl)pyrazol-5-yl]formimidate, aminoacetaldehyde diethyl acetal, and commercial absolute ethanol at ambient room temperature for about two hours. At the end of that time the reaction product mixture is filtered. The solid material obtained is recrystallized from dimethylformamide to yield a crystalline product having a melting point of about 160°–164° C. The product is identified by elemental analyses and NMR spectrum as 4-imino-1-methyl-3-(1-methyl-5-nitroimidazol-2-yl)-1H-pyrazolo[3,4-d]pyrimidine-5(4H)-acetaldehyde, diethyl acetal.

The acid addition salts of the novel compounds are prepared by methods well known to those skilled in the art. The preparation of the hydrogen chloride salt, for example, is generally carried out by suspending or dissolving the substituted pyrazolo pyrimidine in dry ethyl ether, cooling the mixture to about 0° C. in an ice and water bath, and bubbling hydrogen chloride into the mixture for about 15 minutes, while maintaining the temperature of the mixture at about 0° C. At the end of that time, the flask containing the reaction product mixture is stoppered and maintained at about 0° C. for about 1 hour. The mixture is then filtered to isolate the solid material, which is analytically pure, and is identified by melting point, elemental analyses, and NMR spectrum.

The preparation of the nitric, sulfuric, or phosphoric acid addition salts of the novel compounds is generally carried out by suspending or dissolving the substituted pyrazolopyrimidine in a suitable solvent, such as methanol, and adding the sulfuric, nitric, or phosphoric (85% phosphoric) acid dropwise to the mixture with stirring. The mixture is then stirred at ambient room temperature for an additional one to three hours. The mixture is then filtered, and the solid which is collected is washed with methanol. The product is identified by melting point, NMR spectrum, and elemental analyses. Other suitable acid addition salts can be prepared by using acids such as hydrobromic.

The preparation of the intermediate 5-amino-1-methyl-3-(1-methyl-5-nitro-2-imidazolyl)pyrazole-4-carbonitrile, used in the synthesis of the novel compounds of this invention, is taught in copending U.S. application Ser. No. 469,176, filed May 13, 1974 now U.S. Pat. No. 3,947,467.

This intermediate, the 5-amino-1-methyl-3-(1-methyl-5-nitro-2-imidazolyl)pyrazole-4-carbonitrile, is readily synthesized starting from commercially-available 2-methyl-5-nitroimidazole. The 2-methyl-5-nitroimidazole is allowed to react with a suitable alkylating agent, such as dimethyl sulfate, in a suitable solvent, for example benzene, to yield the compound identified as 1,2-dimethyl-5-nitroimidazole. This latter compound is in turn allowed to react with benzaldehyde in the presence of a base, for example sodium ethoxide in absolute ethanol, to yield 1-methyl-5-nitro-2-styrylimidazole.

The next step in the synthesis of the intermediate is the oxidation of the styryl linkage of 1-methyl-5-nitro-2-styrylimidazole. This oxidation can be accomplished by any one of a number of oxidants suitable for oxidizing this type of linkage to the aldehyde (formyl) group.

According to one process, the oxidation can be accomplished by treating the 1-methyl-5-nitro-2-styrylimidazole, suspended in a suitable solvent, with ozone, at about room temperature. Suitable solvents include methanol, methanol and water mixture, or a mixture of methanol, methylene dichloride, and water, and the like.

Another method for oxidizing the styryl compound is taught by Henry et al., U.S. Pat. No. 3,472,864 (Oct. 14, 1969). These authors teach the use of an oxidizing system comprising an alkali metal periodate and osmium tetroxide in a suitable aqueous solvent medium, preferably water and 1,2-dimethoxyethane, at a temperature of from about 20° to 35° C., for a period of about 10 to 20 hours.

The next step in the preparation of the intermediate compound involves allowing the 1-methyl-5-nitroimidazole-2-carboxaldehyde, prepared as described supra, to react with a substituted hydrazine of the formula H$_2$N—NHR, wherein R represents C$_1$–C$_3$ alkyl or hydroxy(C$_1$C$_3$)alkyl. The reaction is carried out in a suitable solvent such as chloroform, at reflux temperature, to yield a 1-methyl-5-nitroimidazole-2-carboxaldehyde alkyl or substituted-alkyl hydrazone. Suitable substituted hydrazines for use in this reaction include methyl hydrazine, ethyl hydrazine, n-propyl hydrazine, isopropyl hydrazine, 2-hydroxyethyl hydrazine, and the like. The reaction conditions are the same for all the hydrazines. Thus, for example, when methyl hydrazine is allowed to react with 1-methyl-5-nitroimidazole-2-carboxaldehyde in chloroform solvent, there is obtained 1-methyl-5-nitroimidazole-2-carboxaldehyde methyl hydrazone.

The hydrazone formed in this manner is in turn allowed to react with N-bromosuccinimide at about room temperature in a suitable solvent, such as chloroform, to yield 1-methyl-5-nitroimidazole-2-carbonyl bromide alkyl or substituted-alkyl hydrazone. The reaction with N-bromosuccinimide is applicable to any of the substituted hydrazones to yield the bromo-substituted hydrazones. As a specific example, when 1-methyl-5-nitroimidazole-2-carboxaldehyde methyl hydrazone is allowed to react with N-bromosuccinimide at room temperature in chloroform solvent, there is obtained 1methyl- 5-nitroimidazole-2-carbonyl bromide methyl hydrazone.

This bromo-substituted hydrazone is unstable and has vesicant and lachrimatory properties. It is therefore used immediately without isolation or extensive purification. The bromo-substituted hydrazone is suspended in a suitable solvent, for example absolute methanol, and malononitrile is added thereto. To the mixture thus formed is added triethylamine dissolved in absolute methanol, while the temperature of the reaction mixture is maintained at about 10°–20° C. by suitable cooling means. This reaction is slightly exothermic and some cooling is required to maintain the desired temperature. As the reaction proceeds, the initial yellow suspension dissolves and is replaced by another suspension during a period of about 1 to about 2 hours. The solid material in this second suspension is the desired product, and is filtered off, washed with methanol and then with water, and dried. For example, when 1-methyl-5-nitroimidazole-2-carbonyl bromide methyl hydrazone is used, this solid material is identified by elemental analyses and NMR spectrum as 5-amino-1-methyl-3-(1-methyl-5-nitro-2-imidazolyl)pyrazole-4-carbonitrile.

The haloalkyl imidazolyl pyrazoles, such as 5-amino-1-(haloalkyl)-3-(1-methyl-5-nitro-2-imidazolyl)-pyrazole-4-carbonitrile, are prepared by reacting the corresponding hydroxyalkyl compound with a halogenating agent such as phosphorus trichloride, phosphorus tribromide, phosphorus trifluoride, thionyl chloride and the like. Thus, 5-amino-1-(β-hydroxyethyl)-3-(1-methyl-5-nitro-2-imidazolyl)pyrazole-4-carbonitrile, is allowed to react with thionyl chloride in an inert solvent such as benzene, in the presence of a small amount of dimethylformamide to yield 5-amino-1-(β-chloroethyl)-3-(1-methyl-5-nitro-2-imidazolyl)pyrazole-4-carbonitrile.

The other intermediates, the formimidates, are obtained by allowing 5-amino-1-methyl-3-(1-methyl-5-nitro-2-imidazolyl)pyrazole-4-carbonitrile, prepared as described above, to react with ortho esters such as trimethyl orthoformate, triethyl orthoformate, tri(n-butyl) orthoformate, or the like, in the presence of a small amount of acetic anhydride. Other ortho esters which can be reacted with any of the 5-aminopyrazole-4-carbonitriles include triallyl orthoformate, tri(2-chloroethyl) orthoformate, triisobutyl orthoformate, tri(2-ethylhexyl) orthoformate, and the like. Thus, for example, when the reactants are 5-amino-1-methyl-3-(1-methyl-5-nitro-2-imidazolyl)pyrazole-4-carbonitrile, trimethyl orthoformate, and a small amount of acetic anhydride, the product obtained is methyl N-[4-cyano-1-methyl-3-(1-methyl-5-nitro-2-imidazolyl)-pyrazol-5-yl]formimidate.

The following Preparations illustrate the synthesis of the intermediate compounds used in making the novel compounds of this invention.

PREPARATION 1

5-Amino-1-methyl-3-(1-methyl-5-nitro-2-imidazolyl)-pyrazole-4-carbonitrile

To a solution of 5 g. (0.0394 mole) of 2-methyl-5-nitroimidazole in 100 ml. of refluxing benzene, there was added, dropwise, a solution of 5 g. (0.0394 mole) of dimethyl sulfate in 10 ml. of benzene. The reaction mixture was allowed to reflux overnight. It was then cooled and there was added dropwise a solution of 6 g. of potassium carbonate in 6 ml. of water. The mixture was stirred for 1 hour and filtered. The organic and aqueous layers of the filtrate were separated and the aqueous layer was extracted with 2 × 50 ml. portions of benzene. The benzene extract was combined with the original organic layer and dried over anhydrous magnesium sulfate. The drying agent was filtered off. The filtrate was concentrated in vacuo to yield product having a melting point of about 135° to 138° C. It was identified as 1,2-dimethyl-5-nitroimidazole. Weight = 4 g.

In a 10-liter round-bottom flask equipped with mechanical stirrer, reflux condenser, and dropping funnel, there was placed 705 g. (5.0 moles) of 1,2-dimethyl-5-nitroimidazole and 3.75 liters of absolute ethanol. Solution was accomplished with stirring. To the solution thus prepared, 685 g. (6.5 moles) of benzaldehyde was added rapidly. To this mixture was rapidly added 150 g. of sodium dissolved in 2.5 l. of methanol, the addition being carried out at room temperature. The reaction mixture was stirred and heated to about 70° C. for a period of about 90 minutes. At a temperature of 40° C., the color changed to dark brown. At the end of the 90 minutes, the reaction product mixture was allowed to cool for 90 minutes, by immersing the reaction vessel in an ice water bath. A precipitate formed. The brown mixture was filtered. The crystalline product was washed four times with a mixture of ice, water, and ethanol, in a 1:1:1 ratio using one liter of the mixture. The crystalline product was air dried at 100° C. It was identified as 1-methyl-5-nitro-2-styrylimidazole. It had a melting point of about 191°–192° C. Weight = 582 g.

In a three-neck, round-bottom, 5-liter flask equipped with a stirrer and gas introduction tube, there was prepared a solution of 454 g. (2.0 moles) of 1-methyl-5-nitro-2-styrylimidazole in a mixture of 2.5 liters of methanol, 1.5 liters of dichloromethane, and 200 ml. of water. The flask was maintained at room temperature by means of a water bath. A mixture of ozone and oxygen (3 percent $O_3$ at 1.1 liters per minute) was passed through the solution. The formation of the ozonide was monitored at intervals by gas-liquid chromatography (GLC) and thin-layer chromatography (TLC). The total ozonolysis time was about 25 hours, at the end of which time the solution had turned a pale yellow color.

A solution of 594 g. of sodium iodide in 2 liters of water and 400 ml. of acetic acid was stirred in a round-bottom, 10-liter flask while the ozonolysis solution was poured in fairly rapidly, keeping the temperature below 40° C. by means of an ice water bath. After stirring the mixture for about 10 minutes, a solution of sodium metabisulfite (192 g. in 2 liters of water) was added to remove the free iodine and cause the resultant solution to turn yellow. The mixture was stirred for about another hour. The mixture was then filtered and the yellow crystals discarded. The filtrate was concentrated in vacuo to about one-third its volume and neutralized to a pH of 6.5 by the addition of solid sodium bicarbonate with stirring. This required about 300 g. of the sodium bicarbonate. The mixture was extracted with 4 × 700 ml. portions of ethyl acetate. The combined ethyl acetate extracts were dried over anhydrous magnesium sulfate for about one-half hour. The drying agent was filtered off and the filtrate concentrated in vacuo to yield a sticky solid. This solid was taken up in about 2.5 liters of n-hexane and the mixture refluxed for about 15 minutes. The residual brown solid was removed by filtration. On cooling, the filtrate deposited yellow crystals which were filtered off and dried in vacuo at 40° C. The filtrate was repeatedly used to reflux the residual brown solid from above in the same manner as before until four such extractions were carried out. There was obtained a total of about 146 g. of product having a melting point of about 81°–83° C., and identified as 1-methyl-5-nitroimidazole-2-carboxaldehyde.

A mixture of 23.5 g. (0.152 mole) of 1-methyl-5-nitroimidazole-2-carboxaldehyde and 7.0 g. (0.152 mole) of methyl hydrazine in 300 ml. of chloroform was boiled under reflux for about 2 hours. The reaction product mixture was evaporated to dryness to yield a bright yellow solid weighing about 25.5 g. A small sample crystallized from ethanol had a melting point of about 175° C. It was identified as 1-methyl-5-nitroimidazole-2-carboxaldehyde methyl hydrazone.

To a stirred solution of 23.5 g. (0.128 mole) of 1-methyl-5-nitroimidazole-2-carboxaldehyde methyl hydrazone in 200 ml. of chloroform, there was added slowly, at room temperature, 22.9 g. (0.128 mole) of N-bromosuccinimide. The reaction was slightly exothermic and the internal temperature was kept below 30° C. by occasional external cooling. After stirring for about 2 hours, the solvent chloroform was removed in vacuo and the residue extracted with 5 × 100 ml. of hot carbon tetrachloride. The insoluble residue was discarded and the combined carbon tetrachloride extracts were concentrated to give a bright yellow solid, identified as 1-methyl-5-nitroimidazole-2-carbonyl bromide methyl hydrazone. Thin-layer chromatography showed the compound was almost pure. Yield 31.0 g.

This compound is unstable and has vesicant and lachrimatory properties. It was used immediately without further purification in the next step of the preparation.

The bromo hydrazone thus prepared, 31.0 g. (0.118 mole), was suspended in 250 ml. of absolute methanol, and 7.80 g. (0.118 mole) of redistilled malononitrile was added. To the mixture was added dropwise a solution of 12 g. (0.118 mole) of triethylamine in 25 ml. of methanol, while maintaining the reaction mixture at a temperature of about 10°–20° C. The reaction was slightly exothermic.

The initial yellow suspension dissolved and was replaced by another suspension during a period of about 1 to 2 hours. At the end of that time, the reaction product mixture was filtered and the solid material collected. The solid was washed with methanol, and then with water, and dried. This solid product had a melting point greater than 300° C. and weighed about 23 g. It was identified as 5-amino-1-methyl-3-(1-methyl-5-nitro-2-imidazolyl)pyrazole-4-carbonitrile. The product was analytically pure as isolated.

PREPARATION 2

5-Amino-1-(2-hydroxyethyl)-3-(1-methyl-5-nitro-2-imidazolyl)-pyrazole-4-carbonitrile A mixture of 15.5 g. (0.1 mole) of 1-methyl-5-nitro-2-imidazolecarboxaldehyde and 7.6 g. (0.1 mole) of 2-hydroxyethyl hydrazine in 300 ml. of chloroform was boiled under reflux for about 2 hours. The reaction product mixture was evaporated to dryness under vacuum to yield product weighing 21.3 g. and having a melting point of about 122°–129° C. This product was identified as 1-methyl-5-nitro-2-imidazolecarboxaldehyde 2-hydroxyethyl hydrazone. A small sample recrystallized from water had a melting point of about 136°–140° C.

To a stirred solution of 21.3 g. (0.1 mole) of 1-methyl-5-nitro-2imidazolecarboxaldehyde 2-hydroxyethyl hydrazone (prepared above) in 200 ml. of chloroform, there was added in small portions, while keeping the temperature below 30° C., 17.8 g. (0.1 mole) of N-bromosuccinimide. The reaction mixture was stirred for about 3 hours at about 25° C. The reaction product mixture was concentrated in vacuo and the residue was extracted eight times with 500 ml. portions of hot carbon tetrachloride. The combined carbon tetrachloride extracts were concentrated in vacuo to yield a bright yellow solid, identified as 1-methyl-5-nitroimidazole-2-carbonyl bromide 2-hydroxyethyl hydrazone. The product had a melting point of about 85°–94° C., and weighed 20.7 g.

The bromo hydrazone thus prepared, 20.7 g. (0.071 mole), was suspended in 150 ml. of anhydrous methanol and 4.7 g. (0.071 mole) of malononitrile was added. To the mixture was added dropwise a solution of 7.3 g. of triethylamine in 15 ml. of absolute methanol, while maintaining the reaction temperature at about 10°–20° C. with an ice water bath.

A dense precipitate formed which was filtered off after about 1 hour and washed with a small amount of commercial absolute ethanol. The material had a melting point of about 242°–243° C., and was identified by elemental analyses and NMR spectrum as 5-amino-1-(2-hydroxyethyl)-3-(1-methyl-5-nitro-2-imidazolyl)-pyrazole-4-carbonitrile.

PREPARATION 3

5-Amino-1-(2-chloroethyl)-3-(1-methyl-5-nitro-2-imidazolyl)-pyrazole-4-carbonitrile A mixture of 1 g. of 5-amino-1-(2-hydroxyethyl)-3-(1-methyl-5-nitro-2-imidazolyl)pyrazole-4-carbonitrile (prepared above), 25 ml. of thionyl chloride, two drops of dimethylformamide, and 5 ml. of benzene was heated and refluxed for about 24 hours. The reaction product mixture was concentrated in vacuo to yield a red gum as a residue. This residue was triturated with commercial absolute ethanol to give a yellow solid weighing about 0.7 g. and having a melting point of about 226°–228° C. It was identified by elemental analyses and NMR spectrum as 5-amino-1-(2-chloroethyl)-3-(1-methyl-5-nitro-2-imidazolyl)pyrazole-4-carbonitrile.

PREPARATION 4

5-Amino-1-ethyl-3-(1-methyl-5-nitro-2-imidazolyl)pyrazole-4-carbonitrile

A mixture of 5.0 g. (0.0322 mole) of 1-methyl-5-nitroimidazole-2-carboxaldehyde, 3.4 g. (0.0322 mole) of ethyl hydrazine oxalate and 3.3 g. (0.322 mole) of triethylamine in 100 ml. of chloroform was refluxed for about 24 hours. The reaction product mixture was cooled, slurried with about 25 ml. of water and the mixture filtered to yield a yellow solid. Thin-layer chromatography of a sample of the yellow solid using ethyl acetate-benzene in 1:1 ratio showed one main yellow spot plus two faster moving trace impurities. The product, 1-methyl-5-nitroimidazole-2-carboxaldehyde ethyl hydrazone, was used without further purification.

To a stirred mixture of 6.8 g. (0.0322 mole) of 1-methyl-5-nitroimidazole-2-carboxaldehyde ethyl hydrazone and 100 ml. of chloroform, was added portionwise 5.8 g. (0.0322 mole) of N-bromosuccinimide, while keeping the temperature of the reaction mixture at less than 30° C. After stirring at ambient room temperature for about 3 hours, the reaction product mixture was concentrated in vacuo. The residue which was obtained was extracted three times with 250 ml. portions of hot carbon tetrachloride. The combined carbon tetrachloride extracts were concentrated in vacuo to yield a yellow solid which weighed 6.3 g. This compound, 1-methyl-5-nitroimidazole-2-carbonyl bromide ethyl hydrazone, was used without purification in the next step of the preparation.

The bromo hydrazone thus prepared, 6.3 g. (0.0228 mole) was suspended in 75 ml. of absolute methanol, and 1.5 g. (0.0228 moles) of malononitrile was added portionwise. The temperature was maintained at about 10°–20° C. using an ice water bath. After addition was complete, the reaction product mixture was stirred for about 1 hour at ambient room temperature. The reaction product mixture was filtered. The solid material which was recovered was recrystallized from dimethylformamide to yield a yellow solid weighing 2.3 g., having a melting point of about 284°–285° C., and identified by elemental analyses and NMR spectrum as 5-amino-1-ethyl-(1-methyl-5-nitro-2-imidazolyl)-pyrazole-4-carbonitrile.

PREPARATION 5

Methyl N-[4-cyano-1-methyl-3-(1-methyl-5-nitro-2-imidazolyl)-pyrazol-5-yl]formimidate A mixture of 1 g. of 5-amino-1-methyl-3-(1-methyl-5-nitro-2-imidazolyl)pyrazole-4-carbonitrile, 12 ml. of trimethyl orthoformate, and 1 ml. of acetic anhydride was refluxed for about 24 hours, and allowed to cool. The reaction product mixture was filtered. The solid material which was filtered off was recrystallized from commercial absolute ethanol to yield product having a melting point of about 184°–185° C. The product was identified by elemental analyses and NMR spectrum as methyl N-[4-cyano-1-methyl-3-(1-methyl-5-nitro-2-imidazolyl)-pyrazol-5-yl]formimidate.

Following the same general procedure as set forth in Preparation 5, and using the appropriate starting materials, the following additional homologous formimidate intermediates were prepared:

Butyl N-[4-cyano-1-methyl-3-(1-methyl-5-nitro-2-imidazolyl)pyrazol-5-yl]formimidate, having a melting point of about 120°–121° C. Identified by elemental analyses and NMR spectrum.

Allyl N-[4-cyano-1-methyl-3-(1-methyl-5-nitro-2-imidazolyl)pyrazol-5-yl]formimidate, having a melting point of about 131°–133° C. Identified by elemental analyses and NMR spectrum.

2-Chloroethyl N-[4-cyano-1-methyl-3-(1-methyl-5-nitro-2-imidazolyl)pyrazol-5-yl]formimidate, having a melting point of about 169°–171° C. Identified by elemental analyses.

Isobutyl N-[4-cyano-1-methyl-3-(1-methyl-5-nitro-2-imidazolyl)pyrazol-5-yl]formimidate, having a melting point of about 134°–136° C. Identified by elemental analyses.

2-Ethylhexyl N-[4-cyano-1-methyl-3-(1-methyl-5-nitro-2-imidazolyl)pyrazol-5-yl]formimidate, having a melting point of about 93°–94° C. Identified by elemental analyses.

The following Examples illustrate the synthesis of the novel compounds of the invention, but the scope of the invention is not to be considered as limited thereby. The syntheses are carried out utilizing the intermediate compounds described in the Preparations set forth hereinabove.

EXAMPLE 1

1-Methyl-3-(1-methyl-5-nitroimidazol-2-yl)-1H-pyrazolo[3,4-d]-pyrimidin-4(5H)-one A mixture of 1.0 g. of 5-amino-1-methyl-3-(1-methyl-5-nitro-2-imidazolyl)pyrazole-4-carbonitrile and 25 ml. of 90 percent formic acid was refluxed for about 2 hours. The reaction product mixture was cooled and the solvent removed in vacuo. The residue, which weighed 1.2 g., was recrystallized from dimethylformamide to yield product having a melting point of about 291°–292° C., and identified by elemental analyses and NMR spectrum as 1-methyl-3-(1-methyl-5-nitroimidazol-2-yl)-1H-pyrazolo[3,4-d]pyrimidin-4-(5H)-one.

EXAMPLE 2

6-Ethyl-1,5-dihydro-1-methyl-3-(1-methyl-5-nitroimidazol-2-yl)-4H-pyrazolo[3,4-d]pyrimidin-4-one A mixture of 1.0 g. of 5-amino-1-methyl-3-(1-methyl-5-nitro-2-imidazolyl)pyrazole-4-carbonitrile and 25 ml. of propionic anhydride was refluxed for about 24 hours and cooled. The dark solution slowly deposited crystals. The crystals were recrystallized from commercial absolute ethanol to yield product having a melting point of about 243°–245° C., and identified by elemental analyses as 6-ethyl-1,5-dihydro-1-methyl-3-(1-methyl-5-nitroimidazol-2-yl)-4-H-pyrazolo[3,4-d]-pyrimidin-4-one.

EXAMPLE 3

6-(Chloromethyl)-6,7-dihydro-6-hydroxy-1-methyl-3-(1-methyl-5-nitroimidazol-2-yl)-1H-pyrazolo[3,4-d]pyrimidin-4-(5H)-one, chloroacetate ester A mixture of 1.0 g. of 5-amino-1-methyl-3-(1-methyl-5-nitro-2-imidazolyl)pyrazole-4-carbonitrile, 3.5 g. of chloroacetic anhydride, 10 drops of concentrated sulfuric acid, and 20 ml. of benzene was refluxed for about 24 hours. The reaction product mixture was cooled and filtered to yield a crude solid. This solid was recrystallized from commercial absolute ethanol to yield white crystals having a melting point of about 217°–218° C., with dec., and identified by elemental analyses and NMR spectrum as 6-(chloromethyl)-6,7-dihydro-6-hydroxy-1-methyl-3-(1-methyl-5-nitroimidazol-2-yl)-1H-pyrazolo[3,4-d]pyrimidin-4(5H)-one, chloroacetate ester.

EXAMPLE 4

4-Amino-1-methyl-3-(1-methyl-5-nitroimidazol-2-yl)-1H-pyrazolo-[3,4-d]pyrimidine A mixture of 2 g. of methyl N-[4-cyano-1-methyl-3-(1-methyl-5-nitro-2-imidazolyl)pyrazol-5-yl]formimidate, 20 ml. of absolute ethanol, and 10 ml. of concentrated ammonium hydroxide was refluxed for about 1 hour. The reaction product mixture was cooled and filtered to yield a yellow solid. The solid was recrystallized from dimethylformamide to yield product having a melting point of about 317°–318° C., with dec., and identified by infrared and NMR spectra, as well as elemental analyses, as 4-amino-1-methyl-3-(1-methyl-5-nitroimidazol-2-yl)-1H-pyrazolo[3,4-d]pyrimidine.

4a. The hydrochloride salt of this compound was prepared as follows:

A mixture of 1.0 g. of 4-amino-1-methyl-3-(1-methyl-5-nitroimidazol-2-yl)-1H-pyrazolo[3,4-d]pyrimidine and 70 ml. of dry ether was prepared and hydrogen chloride was bubbled through the mixture for about 15 minutes while cooling the mixture in an ice and water bath about 0° C., during which time the yellow suspension changed in color to pink. The reaction product mixture was stoppered and allowed to stand for about 1 hour at 0° C. The mixture was filtered to yield pale pink crystals having a melting point of about 268°–269° C., dec., and weighing about 1.2 g. The product was identified by elemental analyses and NMR spectrum as 4-amino-1-methyl-3-(1-methyl-5-nitroimidazol-2-yl)-1H-pyrazolo[3,4-d]pyrimidine hydrochloride.

4b. The sulfate salt of this compound was prepared as follows:

To 1.0 g. of 4-amino-1-methyl-3-(1-methyl-5-nitroimidazol-2-yl)-1H-pyrazolo[3,4-d]pyrimidine suspended in 25 ml. of methanol, there was added dropwise 0.72 g. of concentrated sulfuric acid. The mixture was stirred at ambient room temperature for about 2 to 3 hours. The reaction product mixture was filtered. The solid obtained had a melting point of about 222°–229° C., and was identified by elemental analyses and NMR and IR spectra as 4-amino-1-methyl-3-(1-methyl-5-nitroimidazol-2-yl)-1H-pyrazolo[3,4-d]pyrimidine sulfate.

EXAMPLE 5

4,5-Dihydro-4-imino-1-methyl-3-(1-methyl-5-nitroimidazol-2-yl)-5-propyl-1H-pyrazolo[3,4-d]pyrimidine A mixture of 1.0 g. of methyl N-[4-cyano-1-methyl-3-(1-methyl-5-nitro-2-imidazolyl)pyrazol-5-yl]formimidate, 5 ml. of n-propylamine, and 10 ml. of ethanol was stirred at ambient room temperature for about 10 minutes. The reaction product mixture was filtered and the solid which was recovered was recrystallized from dimethylformamide to yield a product having a melting point of about 239°–240° C. The product was identified by NMR spectrum and elemental analyses as 4,5-dihydro-4-imino-1-methyl-3-(1-methyl-5-nitroimidazol-2-yl)-5-propyl-1H-pyrazolo-[3,4-d]pyrimidine.

5a. The hydrochloride salt of the above compound was prepared as follows:

A suspension of 0.45 g. of 4,5-dihydro-4-imino-1-methyl-3-(1-methyl-5-nitroimidazol-2-yl)-5-propyl-1H-pyrazolo-[3,4-d]pyrimidine was prepared in 65 ml. of anhydrous ethyl ether, and dry hydrogen chloride was bubbled through the stirred mixture at 0° C. for about 15 minutes. The flask was then stoppered and stored at 0° C. for about 1 hour. The mixture was then filtered to yield 0.4 g. of solid having a melting point of about 230°–231° C. The solid was identified by elemental analyses as 4,5-dihydro-4-imino-1-methyl-3-(1-methyl-5-nitroimidazol-2-yl)-5-propyl-1H-pyrazolo[3,4-d]pyrimidine hydrochloride.

Other acid addition salts of the compound of Example 5 were prepared following the general procedure of Example 4b, and using the appropriate acids:

5b. 4,5-Dihydro-4-imino-1-methyl-3-(1-methyl-5-nitroimidazol-2-yl)-5-propyl-1H-pyrazolo[3,4-d]pyrimidine mononitrate, having a melting point of about 209°–212° C. Identified by NMR spectrum and elemental analyses.

5c. 4,5-Dihydro-4-imino-1-methyl-3-(1-methyl-5-nitroimidazol-2-yl)-5-propyl-1H-pyrazolo[3,4-d]pyrimidine monosulfate, having a melting point of about 255°–257° C. Identified by elemental analyses.

EXAMPLE 6

N-[1-Methyl-3-(1-methyl-5-nitroimidazol-2-yl)-1H-pyrazolo[3,4-d]pyrimidin-4-yl]glycine A mixture of 1.0 g. of methyl N-[4-cyano-1-methyl-3-(1-methyl-5-nitro-2-imidazolyl)pyrazol-5-yl]formimidate, 0.3 g. of glycine, 0.4 g. of sodium carbonate, 20 ml. of ethanol, and 20 ml. of water was refluxed for about 1.5 hours. The reaction product mixture was cooled and filtered to yield a crude product. The product was dissolved in hot water, cooled, and the solution acidified with concentrated sulfuric acid to yield a blue-gray precipitate. This precipitate was filtered off and recrystallized from dimethylformamide to yield a product having a melting point of about 240°–241° C. The product was identified by elemental analyses and NMR spectrum as N-[1-methyl-3-(1-methyl-5-nitroimidazol-2-yl)-1H-pyrazolo[3,4-d]pyrimidin-4-yl]glycine.

Following the same general procedure set forth in Example 6 and using appropriate starting materials, the following additional compound was prepared:

N-[1-Methyl-3-(1-methyl-5-nitroimidazol-2-yl)-1H-pyrazolo[3,4-d]pyrimidin-4-yl]methionine, having a melting point of about 207°–208° C. (dec.). Identified by NMR spectrum and elemental analyses.

EXAMPLE 7

5-Ethyl-4,5-dihydro-4-imino-1-methyl-3-(1-methyl-5-nitroimidazol-2-yl)-1H-pyrazolo[3,4-d]pyrimidine A mixture of 1.0 g. of methyl N-[4-cyano-1-methyl-3-(1-methyl-5-nitro-2-imidazolyl)pyrazol-5-yl]formimidate, 10 ml. of a 70 percent aqueous ethylamine solution, and 20 ml. of ethanol was refluxed for about 24 hours. The reaction product mixture was cooled and filtered to yield a pale green solid. The solid was recrystallized from pyridine to yield product having a melting point of about 279°–281° C. The product was identified by infrared spectrum as 5-ethyl-4,5-dihydro-4-imino-1-methyl-3-(1-methyl-5-nitroimidazol-2-yl)-1H-pyrazolo[3,4-d]-pyrimidine.

EXAMPLE 8

5-[2-(Dimethylamino)ethyl]4,5-dihydro-4-imino-1-methyl-3-(1-methyl-5-nitroimidazol-2-yl)-1H-pyrazolo[3,4-d]pyrimidine A mixture of 1.0 g. of methyl N-[4-cyano-1-methyl-3-(1-methyl-5-nitro-2-imidazolyl)pyrazol-5-yl]formimidate, 0.6 g. of unsymmetrical dimethylethylenediamine, and 30 ml. of ethanol was stirred at room temperature for about 1 hour. The reaction product mixture was filtered and the solid which was recovered was crystallized from dimethylformamide to yield product having a melting point of about 192°–194° C. The product was identified by elemental analyses and NMR spectrum as 5-[2-(dimethylamino)-ethyl]-4,5- dihydro-4-imino-1-methyl-3-(1-methyl-5-nitroimidazol-2-yl)-1H-pyrazolo[3,4-d]pyrimidine.

Following the general procedure of Example 8, and using appropriate starting materials, additional novel compounds were prepared, as listed below.

8a. 5-[2-(Diethylamino)ethyl]-4,5-dihydro-4-imino-1-methyl-3-(1-methyl-5-nitroimidazol-2-yl)-1H-pyrazolo[3,4-d]-pyrimidine, having a melting point of about 146°-148° C. Identified by elemental analyses and NMR spectrum.

8b. 4,5-Dihydro-4-imino-1-methyl-3-(1-methyl-5-nitroimidazol-2-yl)-1H-pyrazolo[3,4-d]pyrimidine-5-ethanol, having a melting point of about 272°-274° C. Identified by elemental analyses.

8c. 4,5-Dihydro-4-imino-1-methyl-3-(1-methyl-5-nitroimidazol-2-yl)-5-(9-octadecenyl)-1H-pyrazolo[3,4-d]pyrimidine, having a melting point of about 110°-114° C. Identified by elemental analyses.

8d. 4,5-Dihydro-4-imino-1-methyl-3-(1-methyl-5-nitroimidazol-2-yl)-5-(4-pyridylmethyl)-1H-pyrazolo[3,4-d]pyrimidine, having a melting point of about 256°-258° C. Identified by elemental analyses and NMR spectrum.

8e. 4,5-Dihydro-4-imino-1-methyl-3-(1-methyl-5-nitroimidazol-2-yl)-5-(2-pyridylmethyl)-1H-pyrazolo[3,4-d]-pyrimidine, having a melting point of about 248°-249° C. dec. Identified by elemental analyses and NMR and IR spectrra.

8f. 4,5-Dihydro-4-imino-1-methyl-3-(1-methyl-5-nitroimidazol-2-yl)-5-(3-pyridylmethyl)-1H-pyrazolo[3,4-d]-pyrimidine, having a melting point of about 231°-233° C. Identified by NMR and IR spectra and elemental analyses.

Using the base (8) prepared hereinabove, the following acid addition salt, identified as 8g, was prepared:

8g. A suspension of 0.6 g. of 5-[2-(dimethylamino)-ethyl]-4,5-dihydro-4-imino-1-methyl-3-(1-methyl-5-nitroimidazol-2-yl)-1H-pyrazolo[3,4-d]pyrimidine was prepared in 50 ml. of anhydrous ether, cooled to 0° C. in an ice and water bath, and hydrogen chloride was bubbled through the stirred suspension for about 15 minutes. At the end of that time, the flask was stoppered and the reaction mixture was allowed to stand at 0° C. for about 1 hour. The mixture was then filtered and the solid which was collected on the filter was washed with anhydrous ether to yield an off-white powder having a melting point of about 251°-252° C., dec. The product was identified by elemental analyses and NMR spectrum as 5-[2-(dimethylamino)-ethyl]-4,5-dihydro-4-imino-1-methyl-3-(1-methyl-5-nitroimidazol-2-yl)-1H-pyrazolo[3,4-d]pyrimidine dihydrochloride.

Using the base (8a) prepared above, the following acid addition salts, identified as 8h and 8i were prepared:

8h. 5-[2-(Diethylamino)ethyl]-4,5-dihydro-4-imino-1-methyl-3-(1-methyl-5-nitroimidazol-2yl)-1H-pyrazolo[3,4-d]-pyrimidine diphosphate, having a melting point of about 154°-166° C. Identified by elemental analyses and NMR spectrum.

8i. 5-[2-(Diethylamino)ethyl]-4,5-dihydro-4-imino-1-methyl-3-(1-methyl-5-nitroimidazol-2-yl)-1H-pyrazolo[3,4-d]-pyrimidine disulfate, having a melting point of about 229°-234° C. Identified by elemental analyses and NMR spectrum.

Using the base (8d) prepared hereinabove, the following acid addition salts, identified as 8j, 8k, and 8l, were prepared:

8j. A mixture of 0.94 g. of 4,5-dihydro-4-imino-1-methyl-3-(1-methyl-5-nitroimidazol-2-yl)-5-(4-pyridylmethyl)-1H-pyrazolo[3,4-d]pyrimidine and 65 ml. of anhydrous ether were cooled to 0° C., with stirring, and dry hydrogen chloride was bubbled through the mixture for about 15 minutes. The flask was then stoppered and stored at 0° C. for about 1 hour. The mixture was filtered to give 1.1 g. of yellow solid having a melting point of about 233°-234° C., dec. The yellow solid was identified by elemental analyses as 4,5-dihydro-4-imino-1-methyl-3-(1-methyl-5-nitroimidazol-2-yl)-5-(4-pyridylmethyl)-1H-pyrazolo[3,4-d]pyrimidine dihydrochloride.

8k. To a suspension of 0.7 g. of 4,5-dihydro-4-imino-1-methyl-3-(1-methyl-5-nitroimidazol-2-yl)-5-(4-pyridylmethyl)-1H-pyrazolo[3,4-d]pyrimidine in 25 ml. of methanol was added 0.9 g. of 85% phosphoric acid. The mixture was stirred for about three hours at ambient room temperature. The reaction product mixture was filtered and the solid on the filter was washed with a small amount of methanol. The solid as recrystallized from methanol to yield product weighing about 0.4 g. and having a melting point of about 198°-202° C. The product was identified by elemental analyses as 4,5-dihydro-4-imino-1-methyl-3-(1-methyl-5-nitroimidazol-2-yl)-5-(4-pyridylmethyl)-1H-pyrazolo[3,4-d]pyrimidine diphosphate.

8l. 4,5-Dihydro-4-imino-1-methyl-3-(1-methyl-5-nitroimidazol-2-yl)-5-(4-pyridylmethyl)-1H-pyrazolo[3,4-d]-pyrimidine dinitrate, having a melting point of about 174°-176° C. Identified by NMR spectrum and elemental analyses.

Using the base (8e) prepared above, the following acid addition salts, identified as 8m and 8n, were prepared:

8m. 4,5-Dihydro-4-imino-1-methyl-3-(1-methyl-5-nitroimidazol-2-yl)-5-(2-pyridylmethyl)-1H-pyrazolo[3,4-d]-pyrimidine dinitrate, having a melting point of about 178°-180° C. Identified by NMR spectrum and elemental analyses.

8n. 4,5-Dihydro-4-imino-1-methyl-3-(1-methyl-5-nitroimidazol-2-yl)-5-(2-pyridylmethyl)-1H-pyrazolo[3,4-d]-pyrimidine disulfate, having a melting point of about 258°-260° C. Identified by elemental analyses and NMR spectrum.

Using the base (8f) prepared above, the following acid addition salts, identified as 8o, 8p, and 8q, were prepared.

8o. 4,5-Dihydro-4-imino-1-methyl-3-(1-methyl-5-nitroimidazol-2-yl)-5-(3-pyridylmethyl)-1H-pyrazolo[3,4-d]-pyrimidine disulfate, having a melting point of about 267°-272° C. Identified by elemental analyses.

8p. 4,5-Dihydro-4-imino-1-methyl-3-(1-methyl-5-nitroimidazol-2-yl)-5-(3-pyridylmethyl)-1H-pyrazolo[3,4-d]-pyrimidine triphosphate, having a melting point of about 183°-184° C. Identified by elemental analyses.

8q. 4,5-Dihydro-4-imino-1-methyl-3-(1-methyl-5-nitroimidazol-2-yl)-5-(3-pyridylmethyl)-1H-pyrazolo[3,4-d]-pyrimidine dinitrate, having a melting point of about 228°-232° C. Identified by NMR spectrum and elemental analyses.

EXAMPLE 9

4-Hydrazino-1-methyl-3-(1-methyl-5-nitroimidazol-2-yl)-1H-pyrazolo[3,4-d]pyrimidine A mixture of 1 g. of methyl N-[4-cyano-1-methyl-3-(1-methyl-5-nitro-2-imidazolyl)pyrazol-5-yl]formimidate, 1 ml. of hydrazine, and 10 ml. of ethanol was stirred for about 1 hour at room temperature. The reaction product mixture was filtered and the solid which was collected was recrystallized from dimethylformamide to yield a yellow solid having a melting point of about 246°–248° C. The product was identified by elemental analyses and NMR spectrum as 4-hydrazino-1-methyl-3-(1-methyl-5-nitroimidazol-2-yl)-1H-pyrazolo[3,4-d]pyrimidine.

Acid addition salts of this compound were prepared as follows:

9a. To a suspension of 0.5 g. of 4-hydrazino-1-methyl-3-(1-methyl-5-nitroimidazol-2-yl)-1H-pyrazolo[3,4-d]-pyrimidine in 25 ml. of methanol was added dropwise 0.4 g. of 85% phosphoric acid and the mixture stirred at ambient room temperature for about two hours. The reaction product mixture was filtered and the solid obtained was washed on the filter with a little methanol. The solid weighed 0.5 g. and had a melting point of about 222°–225° C. The solid was identified by elemental analyses and NMR spectrum as 4-hydrazino-1-methyl-3-(1-methyl-5-nitroimidazol-2-yl)-1H-pyrazolo[3,4-d]-pyrimidine monophosphate.

9b. 4-Hydrazino-1-methyl-3-(1-methyl-5-nitroimidazol-2-yl)-1H-pyrazolo[3,4-d]pyrimidine monosulfate, having a melting point of about 248°–250° C. Identified by NMR spectrum and elemental analyses.

EXAMPLE 10

5-[3-(Dimethylamino)propyl]-4,5-dihydro-4-imino-1-methyl-3-(1-methyl-5-nitroimidazol-2-yl)-1H-pyrazolo[3,4-d]pyrimidine A mixture of 1.5 g. of butyl N-[4-cyano-1-methyl-3-(1-methyl-5-nitro-2-imidazolyl)pyrazol-5-yl]formimidate, 0.93 g. of 3-aminopropyldimethylamine (unsym. dimethylaminopropylenediamine), and 50 ml. of commercial absolute ethanol was refluxed for about 2 hours. The reaction product mixture was cooled and filtered. The solid which was recovered was recrystallized from dimethylformamide to give product having a melting point of about 151°–154° C. The product was identified by elemental analyses as 5-[3-(dimethylamino)propyl]-4,5-dihydro-4-imino-1-methyl-3-(1-methyl-5-nitroimidazol-2-yl)-1H-pyrazolo-[3,4-d]pyrimidine.

10a. A mixture of 0.72 g. of the free base, prepared hereinabove, and 65 ml. of anhydrous ether was held at 0° C. while dry hydrogen chloride was passed into the mixture for about 15 minutes. The flask with its contents was stoppered and allowed to stand for 1 hour at 0° C. The mixture was filtered to yield 1 g. of hygroscopic solid having a melting point of about 266°–268° C. dec. The product was identified by elemental analyses as 5-[3-(dimethylamino)pyropyl]4,5-dihydro-4-imino-1-methyl-3-(1-methyl-5-nitroimidazol-2-yl)-1H-pyrazolo-[3,4-d]pyrimidine dihydrochloride monohydrate.

EXAMPLE 11

N-[1-Methyl-3-(1-methyl-5-nitroimidazol-2-yl)-1H-pyrazolo[3,4-d]-pyrimidin-4-yl]acetamide A mixture of 2.3 g. of 4-amino-1-methyl-3-(1-methyl-5-nitroimidazol-2-yl)-1H-pyrazolo[3,4-d]pyrimidine and 30 ml. of acetic anhydride was refluxed for about 22 hours. The reaction product mixture was cooled and filtered. The solid which was obtained was recrystallized from dimethylformamide to yield product having a melting point of about 284°–286° C. The product was identified by elemental analyses and NMR spectrum as N-[1-methyl-3-(1-methyl-5-nitroimidazol-2-yl)-1H-pyrazolo[3,4-d]-pyrimidin-4-yl]acetamide.

EXAMPLE 12

1,5-Dihydro-1-methyl-3-(1-methyl-5-nitroimidazol-2-yl)-6-(trifluoromethyl)-4H-pyrazolo[3,4-d]pyrimidin-4-one A mixture of 3 g. of 5-amino-1-methyl-3-(1-methyl-5-nitro-2-imidazolyl)pyrazole-4-carbonitrile and 25 ml. of trifluoroacetic anhydride was refluxed overnight to give a solid material. This solid was recrystallized from ethanol to yield two products. The higher melting product had a melting point of about 284°–286° C. It was identified by elemental analyses as 1,5-dihydro-1-methyl-3-(1-methyl-5-nitroimidazol-2-yl)-6-(trifluoromethyl)-4H-pyrazolo[3,4-d]pyrimidin-4-one. The other product, the lower melting product, having a melting point of about 225°–228° C., was identified by elemental analyses as N-[4-cyano-1-methyl-3-(1-methyl-5-nitroimidazol-2-yl)pyrazol-5-yl]-2,2,2-trifluoroacetamide.

EXAMPLE 13

1,5-Dihydro-1,6-dimethyl-3-(1-methyl-5-nitroimidazol-2-yl)-4H-pyrazolo[3,4-d]pyrimidin-4-one A mixture of 5 g. of 5-amino-1-methyl-3-(1-methyl-5-nitro-2-imidazolyl)pyrazole-4-carbonitrile, 10 ml. of concentrated sulfuric acid, and 20 ml. of absolute ethanol was heated to refluxing for about 1 hour. The reaction product mixture was then cooled and 50 ml. of water added thereto. The crude product which precipitated was identified by TLC as 5-amino-1-methyl-3-(1-methyl-5-nitro-2-imidazolyl)pyrazole-4-carboxamide having a melting point of about 249°–250° C. This material was used without further purification.

A mixture of 1 g. of the carboxamide prepared above and 10 ml. of acetic anhydride was heated to refluxing for about 6 hours. The reaction product mixture was concentrated in vacuo. The residue was recrystallyzed from ethanol to yield product having a melting point of about 287°–288° C. with dec. It was identified by elemental analyses as 1,5-dihydro-1,6-dimethyl-3-(1-methyl-5-nitroimidazol-2-yl)-4H-pyrazolo[3,4-d]pyrimidin-4-one.

EXAMPLE 14

4-Imino-1-methyl-3-(1-methyl-5-nitroimidazol-2-yl)-1H-pyrazolo-[3,4-d]pyrimidine-5(4H)-acetaldehyde, diethyl acetal A mixture of 2 g. of methyl N-[4-cyano-1-methyl-3-(1-methyl-5-nitro-2-imidazolyl)pyrazol-5-yl]formimidate, 1.7 g. of aminoacetaldehyde diethyl acetal, and 30 ml. of commercial absolute ethanol was stirred at about ambient room temperature for about 2 hours. At the end of that time the reaction product mixture was filtered. The solid which was collected was recrystallized from dimethylformamide to yield crystalline product having a melting point of about 160°–164° C. The product was identified by elemental analyses and NMR spectrum as 4-imino-1-methyl-3-(1-methyl-5-nitroimidazol-2-yl)-1H-pyrazolo[3,4-d]-pyrimidine-5(4H)-acetaldehyde, diethyl acetal.

EXAMPLE 15

4,5-Dihydro-4-imino-1-methyl-3-(1-methyl-5-nitroimidazol-2-yl)-5-(2-morpholinoethyl)-1H-pyrazolo[3,4-d]pyrimidine dihydrochloride A mixture of 2 g. of methyl N-[4-cyano-1-methyl-3-(1-methyl-5-nitro-2-imidazolyl)pyrazol-5-yl]formimidate, 1.6 g. of N-(2-aminoethyl)morpholine, and 50 ml. of commercial absolute ethanol was stirred at about ambient room temperature for about 1.5 hours. At the end of that time, the reaction product mixture was filtered. The solid which was collected was recrystallized from dimethylformamide to give material having a melting point of about 232°–234° C., and identified by NMR spectrum as 4,5-dihydro-4-imino-1-methyl-3-(1-methyl-5-nitroimidazol-2-yl)-5-(2-morpholinoethyl)-1H-pyrazolo[3,4-d]pyrimidine.

15a. The dihydrochloride salt of the above compound as prepared as follows:

A suspension of 0.8 g. of the compound in 65 ml. of anhydrous ethyl ether was cooled to about 0° C., and held at that temperature while anhydrous hydrogen chloride was bubbled through for about 15 minutes. The flask was then stoppered and allowed to stand at about 0° C. for about 1 hour. The mixture was then filtered to yield 0.9 g. of solid having a melting point of about 256°–257° C. dec. The solid was identified by elemental analyses as 4,5-dihydro-4-imino-1-methyl-3-(1-methyl-5-nitroimidazol-2-yl)-5-(2-morpholinoethyl)-1H-pyrazolo-[3,4-d]pyrimidine dihydrochloride.

Following the general procedure of Example 8i, other acid addition salts of the above base (15) were prepared as follows:

15b. 4,5-Dihydro-4-imino-1-methyl-3-(1-methyl-5-nitroimidazol-2-yl)-5-(2-morpholinoethyl)-1H-pyrazolo[3,4-d]-pyrimidine diphosphate, having a melting point of about 203°–208° C. Identified by NMR spectra and elemental analyses.

15c. 4,5-Dihydro-4-imino-1-methyl-3-(1-methyl-5-nitroimidazol-2-yl)-5-(2-morpholinoethyl)-1H-pyrazolo[3,4-d]-pyrimidine dinitrate, having a melting point of about 183°–185° C. Identified by elemental analyses.

Members of the instant series of novel compounds have demonstrated in vitro activity against a number of organisms, many of which are important animal pathogens. The in vitro antimicrobial activity of the nitroimidazoles has been determined using the tube dilution test.

EXPERIMENT 1

The efficacy of the novel compounds against the bacterium, Escherichia coli, was determined as follows:

This bacterium, *Escherichia coli*, grows readily at titers of about $10^{9.0}$ mcg./ml. (ml. of medium) and produces highly visible growth after a short incubation period. In carrying out the test, a 5.0-mg. sample of the pyrazolopyrimidine was solubilized in 5.0 ml. of dimethylsulfoxide (DMSO). This was then added to 45.0 ml. of sterile Mueller-Hinton broth to give a concentration of 100 mcg./ml. of the compound. A series of two-fold dilutions of this mixture was made in 5.0-ml. amounts using Mueller-Hinton broth as diluent, the final dilutions ranging from 100.0 to 0.78 mcg./ml. A control tube containing 5.0 ml. Mueller-Hinton broth was included. Using a 1.0 ml. pipette, each test tube was inoculated with one drop of a $10^{-4.0}$ dilution of the *E. coli* bacterium prepared in Mueller-Hinton broth. The test tubes were then incubated at about 36° C. for 20–22 hours, and the minimum inhibitory concentration (MIC) of the test compound for that bacterium taken as the concentration which completely prevented visible growth.

The above example serves to illustrate the general test procedure used. As is well known to those skilled in the art, variations in certain parts of the procedure are necessary, depending upon the specific test organism. Thus, in the use of certain bacteria, such as pasteurella, where the growth is relatively light, a less dilute inoculum was used. With certain other bacteria, the incubation time required for growth was considerably longer than 24 hours, namely 36 to 96 hours. Again, such necessary variations in the incubation time required for growth are well known to those skilled in and familiar with biological test procedures. Another variation in the test described above involves the use with certain mycoplasma of a pH change indicator, for example phenol red in the specific mycoplasma media. The inhibition or prevention of growth was detected by the failure of a color change to occur.

The results of tests of representative compounds, identified hereinbelow, are set forth in the table which follows. In the table, Column 1 identifies the test compound; and Columns 2 through 15 give the MIC in mcg./ml. of the individual compounds against the individual test organisms.

The compounds tested are identified by reference to the numbers of the examples describing the preparation of the compounds.

TABLE 1

| Compound | Pseudomonas | Escherichia coli | Salmonella | Pasteurella multocida cattle | Pasteurella multocida turkey | Bordetella | Streptococcus | Staphylococcus | Mycoplasma hyorhinis | Mycoplasma synoviae | Mycoplasma hyosynoviae | Mycoplasma gallisepticum | Vibrio coli | Mycoplasma hyopneumoniae | Hemophilus gallinarum |
|---|---|---|---|---|---|---|---|---|---|---|---|---|---|---|---|
| 1 | >50.0 | 25.0 | 25.0 | 1.56 | 50.0 | >50.0 | >50.0 | >50.0 | 50.0 | 25.0 | >50.0 | 50.0 | 6.25 | 6.25 | |
| 2 | >50.0 | >50.0 | >50.0 | 3.12 | 50.0 | >50.0 | 50.0 | >50.0 | >50.0 | 50.0 | >50.0 | 50.0 | 1.56 | 12.5 | |
| 3 | >50.0 | >50.0 | >50.0 | 3.12 | 50.0 | >50.0 | 50.0 | >50.0 | 50.0 | 50.0 | >50.0 | 50.0 | 50.0 | 12.5 | |
| 4 | >50.0 | >50.0 | >50.0 | 0.19 | 1.56 | >50.0 | >50.0 | >50.0 | 50.0 | 1.56 | | 3.12 | >50.0 | 0.39 | |
| 4a | >50.0 | >50.0 | >50.0 | <0.78 | <0.78 | >50.0 | >50.0 | >50.0 | 50.0 | 1.56 | | >50.0 | 50.0 | >50.0 | |
| 4b | 50.0 | 12.5 | | 6.25 | 6.25 | 50.0 | 50.0 | 25.0 | 3.12 | 50.0 | | 25.0 | | 25.0 | |
| 5 | 50.0 | 50.0 | 50.0 | 0.19 | 3.12 | >50.0 | 6.25 | 12.5 | 6.25 | 0.78 | | 1.56 | 0.19 | 0.78 | |
| 5a | 25.0 | 12.5 | 12.5 | <0.78 | <0.78 | 50.0 | 6.25 | 12.5 | <1.56 | 1.56 | | 3.12 | 1.56 | 1.56 | 12.5 |
| 5b | 12.5 | 12.5 | 25.0 | 1.56 | 1.56 | 25.0 | 12.5 | 12.5 | 6.25 | 3.12 | | 12.5 | | 1.56 | |
| 5c | 12.5 | 12.5 | 50.0 | 3.12 | 1.56 | 25.0 | 12.5 | 12.5 | 6.25 | 3.12 | | 12.5 | | 3.12 | |

TABLE 1-continued

| Compound | Pseudomonas | Escherichia coli | Salmonella | Pasteurella multocida cattle | Pasteurella multocida turkey | Bordetella | Streptococcus | Staphylococcus | Mycoplasma hyorhinis | Mycoplasma synoviae | Mycoplasma hyosynoviae | Mycoplasma gallisepticum | Vibrio coli | Mycoplasma hyopneumoniae | Hemophilus gallinarum |
|---|---|---|---|---|---|---|---|---|---|---|---|---|---|---|---|
| 6 | >50.0 | >50.0 | 50.0 | <0.78 | 6.25 | 50.0 | 12.5 | 25.0 | 3.12 | 6.25 | | <1.56 | <0.78 | 1.56 | |
| 7 | 50.0 | 12.5 | 25.0 | <0.78 | 1.56 | 50.0 | 6.25 | 12.5 | 12.5 | <0.78 | | 12.5 | 3.12 | 1.56 | |
| 8 | 50.0 | 25.0 | 12.5 | <0.78 | 3.12 | 50.0 | <0.78 | 6.25 | 3.12 | <0.78 | | <0.78 | <0.78 | <0.39 | |
| 8a | >50.0 | >50.0 | >50.0 | <0.78 | >50.0 | >50.0 | >50.0 | >50.0 | >50.0 | >50.0 | | 12.5 | >50.0 | >50.0 | >50.0 |
| 8b | 12.5 | 25.0 | 12.5 | <0.78 | 1.56 | >50.0 | 3.12 | 3.12 | 3.12 | 6.25 | | 3.12 | <0.78 | 1.56 | 6.25 |
| 8c | 12.5 | 25.0 | 25.0 | <0.78 | 1.56 | >50.0 | 3.12 | 1.56 | 6.25 | 6.25 | | 3.12 | <1.56 | 1.56 | 25.0 |
| 8e | >50.0 | >50.0 | >50.0 | <0.78 | 6.25 | 50.0 | 25.0 | 25.0 | 6.25 | 12.5 | | 1.56 | <0.78 | | 50.0 |
| 8f | 6.25 | 12.5 | 25.0 | <0.78 | <0.78 | 50.0 | 3.12 | 3.12 | <0.78 | 1.56 | | <0.78 | <0.78 | | 6.25 |
| 8g | 50.0 | 12.5 | 12.5 | <0.78 | 1.56 | 50.0 | 6.25 | 6.25 | 6.25 | <0.78 | | 3.12 | <0.78 | <0.78 | |
| 8h | 12.5 | 50.0 | 50.0 | 1.56 | 6.25 | 50.0 | 6.25 | 12.5 | 0.78 | 1.56 | | 1.56 | | 0.78 | |
| 8i | 50.0 | 6.25 | 50.0 | 6.25 | 3.12 | 50.0 | 12.5 | 12.5 | 3.12 | 3.12 | | 12.5 | | 6.25 | |
| 8k | 3.12 | 12.5 | 12.5 | 0.78 | 3.12 | 50.0 | 3.12 | 3.12 | 0.78 | 3.12 | | 0.78 | | 0.78 | |
| 8l | 50.0 | 50.0 | 25.0 | 6.25 | 6.25 | 50.0 | 50.0 | 50.0 | 3.12 | 6.25 | | 12.5 | | 6.25 | |
| 8m | 12.5 | 25.0 | 25.0 | 3.12 | 3.12 | 25.0 | 6.25 | 6.25 | 1.56 | 3.12 | | 6.25 | | 6.25 | |
| 8n | 50.0 | 50.0 | >50.0 | 0.78 | 3.12 | >50.0 | 6.25 | 6.25 | <0.78 | 3.12 | | <0.78 | | 0.78 | |
| 8o | 25.0 | 50.0 | 25.0 | 3.12 | 1.56 | 50.0 | 3.12 | 6.25 | 1.56 | 3.12 | | 3.12 | | 3.12 | |
| 8p | 50.0 | 25.0 | 50.0 | 3.12 | 3.12 | 50.0 | 12.5 | 12.5 | 1.56 | 3.12 | | 3.12 | | 3.12 | |
| 8q | 12.5 | 50.0 | 25.0 | 6.25 | 6.25 | 50.0 | 6.25 | 6.25 | 6.25 | 6.25 | | 6.25 | | 3.12 | |
| 9 | >50.0 | 6.25 | 6.25 | <0.78 | <0.78 | 25.0 | 1.56 | 6.25 | 1.56 | 6.25 | | <0.78 | <0.78 | | |
| 9a | 50.0 | 50.0 | 50.0 | 3.12 | 1.56 | 50.0 | 3.12 | 6.25 | 1.56 | 12.5 | | 1.56 | | 1.56 | |
| 9b | 50.0 | 50.0 | 25.0 | 1.56 | 1.56 | 50.0 | 3.12 | 6.25 | 1.56 | 12.5 | | 1.56 | | 1.56 | |
| 10 | 25.0 | 6.25 | 6.25 | <0.78 | | 50.0 | <0.78 | 6.25 | <0.78 | <0.78 | | 1.56 | <0.78 | <0.78 | 6.25 |
| 10a | 6.25 | 6.25 | 6.25 | <0.78 | <0.78 | 25.0 | 3.12 | 3.12 | 3.12 | <0.78 | | 1.56 | <1.56 | <0.78 | 6.25 |
| 11 | >50.0 | >50.0 | >50.0 | <0.78 | 3.12 | >50.0 | 25.0 | 12.5 | 12.5 | 12.5 | | 12.5 | 3.12 | 12.5 | 50.0 |
| 12 | | >50.0 | >50.0 | 50.0 | >50.0 | >50.0 | >50.0 | >50.0 | >50.0 | | | >50.0 | >50.0 | | |
| 13 | >50.0 | >50.0 | 25.0 | <0.78 | 6.25 | 12.5 | 25.0 | >50.0 | >50.0 | 50.0 | | 25.0 | <0.78 | >50.0 | |
| 14 | >50.0 | >50.0 | >50.0 | 3.12 | 12.5 | >50.0 | 25.0 | 50.0 | 12.5 | 25.0 | | 12.5 | <0.78 | 25.0 | 50.0 |
| 15a | 50.0 | 12.5 | 25.0 | <0.78 | 1.56 | >50.0 | 3.12 | 6.25 | 3.12 | 3.12 | | <0.78 | <1.56 | <0.78 | 12.5 |
| 15b | 25.0 | 6.25 | 25.0 | 1.56 | 1.56 | 50.0 | 6.25 | 12.5 | 3.12 | 3.12 | | 6.25 | | 1.56 | |
| 15c | 50.0 | 50.0 | 50.0 | 25.0 | 25.0 | 50.0 | 50.0 | 12.5 | 1.56 | 3.12 | | 12.5 | | 3.12 | |

EXPERIMENT 2

The efficacy of the novel compounds against *Pasteurella multocida* infections in mice when administered by injection was studied.

Female Swiss mice weighing from 15 to about 20 g. were used. The test compound, 5.0 mg., was weighed out and dissolved in 0.5 ml. of dimethyl sulfoxide, and this solution was added to 9.5 ml. of sodium carboxymethylcellulose suspension. Groups of five mice each were injected intraperitoneally with 0.1 ml. each of the above-prepared test composition. This preparation gave a test rate of 2.5 mg. per kilo of body weight of mouse. The compounds were tested at 1.25, 2.5, or 5.0 per kilogram of body weight of mouse, and the test preparations for the rates of 1.25 and 5.0 mg./kg. were prepared in a similar manner. Immediately after receiving the test compound, the mice were challenged using $\log_{10}$ dilutions of $10^{-4}$, $10^{-5}$ and $10^{-6}$, of a 16 to 20-hour tryptose broth culture of *Pasteurella multocida* at 0.1 ml. per mouse subcutaneously. Similar groups of non-treated control mice were also challenged, the challenge being administered subcutaneously. The groups of mice were observed daily for mortality and the total mortality in treated groups compared with that which occurred in the nonmedicated control groups. The results are set forth in Chart 1, which follows. Each test compound is identified by the number of the example describing its preparation.

In the chart, column 1 lists the test compound; column 2, the dosage of test compound in mg./kg. of mouse body weight; column 3, the dilution of the challenge organism; and column 4, the ratio of the number of mice surviving the test at each dosage and challenge dilution to the number of mice tested at each dosage and challenge dilution, called the survival ratio.

Table 2

| Cpd. | Dose mg./kg. | Challenge Dilution | Survival Ratio |
|---|---|---|---|
| 2 | 5.0 | $10^{-4}$ | 3/15 |
| | | $10^{-5}$ | 5/15 |
| | | $10^{-6}$ | 5/15 |
| 3 | 5.0 | $10^{-4}$ | 1/20 |
| | | $10^{-5}$ | 4/20 |
| | | $10^{-6}$ | 5/20 |
| | 2.5 | $10^{-4}$ | 3/10 |
| | | $10^{-5}$ | 1/10 |
| | | $10^{-6}$ | 2/10 |
| 4 | 5.0 | $10^{-4}$ | 4/10 |
| | | $10^{-5}$ | 5/10 |
| | | $10^{-6}$ | 5/10 |
| 4a | 5.0 | $10^{-4}$ | 7/10 |
| | | $10^{-5}$ | 7/10 |
| | | $10^{-6}$ | 7/10 |
| 5 | 5.0 | $10^{-4}$ | 3/10 |
| | | $10^{-5}$ | 6/10 |
| | | $10^{-6}$ | 9/10 |
| 6 | 5.0 | $10^{-4}$ | 2/10 |
| | | $10^{-5}$ | 2/10 |
| | | $10^{-6}$ | 2/10 |
| 7 | 5.0 | $10^{-4}$ | 4/10 |
| | | $10^{-5}$ | 7/10 |
| | | $10^{-6}$ | 10/10 |
| | 2.5 | $10^{-4}$ | 1/5 |
| | | $10^{-5}$ | 2/5 |
| | | $10^{-6}$ | 3/5 |
| 8 | 5.0 | $10^{-4}$ | 10/10 |
| | | $10^{-5}$ | 10/10 |
| | | $10^{-6}$ | 10/10 |
| | 2.5 | $10^{-4}$ | 2/5 |
| | | $10^{-5}$ | 3/5 |
| | | $10^{-6}$ | 5/5 |
| | 1.25 | $10^{-4}$ | 1/5 |
| | | $10^{-5}$ | 2/5 |
| | | $10^{-6}$ | 3/5 |
| 8a | 5.0 | $10^{-4}$ | 2/5 |
| | | $10^{-5}$ | 1/5 |
| | | $10^{-6}$ | 5/5 |
| 8d | 5.0 | $10^{-4}$ | 5/5 |
| | | $10^{-5}$ | 5/5 |
| | | $10^{-6}$ | 5/5 |
| 8g | 5.0 | $10^{-4}$ | 7/10 |
| | | $10^{-5}$ | 9/10 |
| | | $10^{-6}$ | 10/10 |
| | 2.5 | $10^{-4}$ | 2/10 |
| | | $10^{-5}$ | 6/10 |
| | | $10^{-6}$ | 10/10 |
| 9 | 5.0 | $10^{-4}$ | 10/10 |

Table 2-continued

| Cpd. | Dose mg./kg. | Challenge Dilution | Survival Ratio |
|---|---|---|---|
|  |  | $10^{-5}$ | 8/10 |
|  |  | $10^{-6}$ | 9/10 |
| 10 | 5.0 | $10^{-4}$ | 5/ 5 |
|  |  | $10^{-5}$ | 4/ 5 |
|  |  | $10^{-6}$ | 5/ 5 |
| 11 | 5.0 | $10^{-4}$ | 0/ 5 |
|  |  | $10^{-5}$ | 0/ 5 |
|  |  | $10^{-6}$ | 1/ 5 |
| 12 | 5.0 | $10^{-4}$ | 1/ 5 |
|  |  | $10^{-5}$ | 1/ 5 |
|  |  | $10^{-6}$ | 0/ 5 |
| 13 | 5.0 | $10^{-4}$ | 1/10 |
|  |  | $10^{-5}$ | 5/10 |
|  |  | $10^{-6}$ | 5/10 |
|  | 2.5 | $10^{-4}$ | 1/ 5 |
|  |  | $10^{-5}$ | 1/ 5 |
|  |  | $10^{-6}$ | 3/ 5 |
| 14 | 5.0 | $10^{-4}$ | 0/ 5 |
|  |  | $10^{-5}$ | 1/ 5 |
|  |  | $10^{-6}$ | 2/ 5 |
| Infected Controls | 0 | $10^{-4}$ | 6/70 |
|  |  | $10^{-5}$ | 16/80 |
|  |  | $10^{-6}$ | 26/90 |

EXPERIMENT 3

A comparison of the in vivo activity of a novel compound of this invention and nitrofurazolidone (Furacin) when administered in drinking water for the treatment of *Pasteurella multocida* infection in mice was conducted. The novel compound of this invention used in this study was 4,5-di-hydro-4-imino-1-methyl-3-(1-methyl-5-nitroimidazol-2-yl)-5-(4-pyridylmethyl)-1H-pyrazolo[3,4-d]pyrimidine diphosphate, identified by its operating example No. 8k. The test was conducted in the following manner.

Twenty white female mice, each weighing about 15–20 g., were divided into four groups of five mice each, and the groups were each placed on water medication containing:
a. Compound 8k, 0.5 g./gal.
b. Compound 8k, 2.0 g./gal.
c. Nitrofurazolidone, 0.5 g./gal.
d. Nitrofurazolidone, 2.0 g./gal.

The groups receiving each treatment were challenged with 0.1 ml. each of a $10^{-4}$, $10^{-5}$, $10^{-6}$, or $10^{-7}$ dilution of a 16 to 20-hour broth culture of *P. multocida*. Untreated groups of mice were challenged with $\log_{10}$ dilutions of the same broth culture using 0.1 ml. of $10^{-4}$ through $10^{-9}$ dilutions. The mice were observed for 7 days, then the $LD_{50}$ for the various treated groups of mice and the $LD_{50}$ for the control group of mice were calculated. By subtracting the $LD_{50}$ of each of the treated groups from that of the control group of mice, there was obtained a figure called the protective index. The higher the protective index in value, the more active the compound was against the infection.

The results are set forth in the table which follows. In the table, column 1 sets forth the treatment; column 2, the $LD_{50}$; and column 3 the $\log_{10}$ protection obtained.

Table 3

| Treatment | Rate g./gal. | $LD_{50}$ | Protective Index |
|---|---|---|---|
| 8i | 2.0 | — | >2.5 |
|  | 0.5 | — | >2.5 |
| Nitrofurazolidone | 2.0 | — | >2.5 |
|  | 0.5 | $10^{-4.3}$ | 2.2 |
| Nonmedicated |  |  |  |

Table 3-continued

| Treatment | Rate g./gal. | $LD_{50}$ | Protective Index |
|---|---|---|---|
| Controls |  | $10^{-6.5}$ | — |

EXPERIMENT 4

The in vitro activity of certain of the novel compounds of this invention against two fish bacterial pathogens was determined using tryptose broth and the standard tube dilution test system. Doubling dilutions ranging from 100.0 to 0.78 mcg./ml. of each of the test compounds were prepared in 5 ml. amounts of tryptose broth. Each tube in the series was then inoculated with one drop from a 24-hour broth culture of either *Pseudomonas* sp. or a strain of *Aeromonas liquefaciens*. The tubes were incubated overnight at about 37° C., and the minimum inhibitory concentration (MIC) determined and recorded.

The results are set forth in Table 4, which follows. Column 1 lists the test compounds identified by their operating example number; column 2 lists the MIC for *Pseudomonas* sp.; and column 3 lists the MIC for *Aeromonas liquefaciens*.

Table 4

| Compound of Example No. | *Pseudomonas* mcg./ml. | *Aeromonas liquefaciens* mcg./ml. |
|---|---|---|
| 2 | 50.0 | 50.0 |
| 5b | 3.12 | 25.0 |
| 8 | 1.56 | 12.5 |
| 8k | 0.78 | 50.0 |
| 9a | 0.78 | 25.0 |
| 15b | 1.56 | 50.0 |

EXPERIMENT 5

A number of representative compounds, namely, 5b, 8, and 15b, were tested for their in vitro activity against *Treponema hyodysenteriae*. The treponema were propagated on blood agar plates. Each plate which was prepared contained 20 ml. of trypticase soy agar (Baltimore Biological Laboratory [BBL]) with 5.0 g./l. of yeast extract (Difco) and 5 percent sterile defibrinated horse blood. The plates were sterile plastic 15 × 100 mm. petri plates. Incubation was carried out at 37° C. for 4 days under anaerobic conditions using the BBL Gas Pak system.

The concentrations of test compounds in this initial test were prepared in dilutions ranging from 2000 mcg./ml. to 7.8 mcg./ml. The test procedure was carried out in the following manner. Five ml. of a twenty-fold concentration in tryptose broth (Difco) of each filter-sterilized test compound dilution was mixed in a series of flasks containing 90 ml. of melted trypticase soy agar with yeast extract. Five ml. of horse blood was then added per flask. The contents of these flasks were then used to prepare a series of blood agar plates in doubling decreasing dilutions ranging from 100 mcg./ml. to 0.39 mcg./ml.

The treponema for inoculation of these plates were obtained by adding 3.0 ml. of sterile tryptose broth to the surface of a plate on which the treponema had been propagated. A sterile cotton-tipped swab was used to loosen the treponema from the agar. This suspension was then diluted 100-fold and each of the plates containing the test compounds was inoculated with 0.01 ml. along with the control plates which did not contain test compounds. The inoculum was spread so that it covered the surface of each plate, a bent sterile plastic pipette being used for this purpose for each plate. The plates were incubated at about 36° C. for about 4 days and then examined for growth of the treponema. The minimum inhibitory concentration (MIC) of each test compound was the concentration that prevented growth of treponema.

These representative compounds all inhibited growth of the treponema at each of the levels tested, and the MIC for these compounds was ≤ 1.56 mcg./ml.

Several of the novel compounds of this invention are active in vivo against *Salmonella typhimurium* in chicks when administered to chickens subcutaneously.

6-Ethyl-1,5-dihydro-1-methyl-3-(1-methyl-5-nitroimidazol-2-yl)-4H-pyrazolo[3,4-d]pyrimidin-4-one 5-[2-(Dimethylamino)ethyl]-4,5-dihydro-4-imino-1-methyl-3-(1-methyl-5-nitroimidazol-2-yl)-1H-pyrazolo[3,4-d]-pyrimidine 1,5-Dihydro-1,6-dimethyl-3-(1-methyl-5-nitroimidazol-2-yl)-4H-pyrazolo[3,4-d]pyrimidin-4-one These compounds can be used to treat *S. typhimurium* in chicks.

Several of the compounds coming within the scope of the generic formula supra are active both in vitro and in vivo against *Trichomonas vaginalis*. These compounds are: 5-[2-(dimethylamino)ethyl]-4,5-dihydro-4-imino-1-methyl-3-(1-methyl-5-nitroimidazol-2-yl)-1H-pyrazolo[3,4-d]pyrimidine, 5-[3-(dimethylamino)propyl]-4,5-dihydro-4-imino-1-methyl-3-(1-methyl-5-nitroimidazol-2-yl)-1H-pyrazolo[3,4-d]pyrimidine, and 6-(chloromethyl)-6,7-dihydro-6-hydroxy-1-methyl-3-(1-methyl-5-nitroimidazol-2-yl)-1H-pyrazolo[3,4-d]pyrimidin-4(5H)-one, chloroacetate ester.

In view of the activities demonstrated by these novel compounds in the tests described above, the compounds of this invention can be used to control *T. vaginalis*, *P. multocida*, and *S. typhimurium* in animals. The compounds are also useful in combatting the fish bacterial pathogens identified as *Pseudomonas sp.* and *Aeromonas liquefaciens*, respectively.

When the novel compounds are used to control *P. multocida* or *T. vaginalis* in animals, the compounds may be formulated as described in Experiment 2, above, and administered by injection. The compounds may also be administered orally, for example, in the drinking water of the animals for the control of *P. multocida*.

The treatment of *S. typhimurium* in chicks is accomplished by incorporating the compound in the normal chick ration and allowing the chicks to feed *ad libitum*. The compound is incorporated in the feed at effective levels, suitably from about 50 g. per ton to about 100 g. per ton of feed.

I claim:

1. A pyrazolo[3,4-d]-pyrimidine compound of the formula

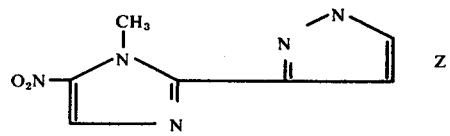

wherein
Z is selected from the group consisting of

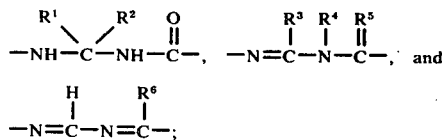

R is $C_1$–$C_3$ alkyl, hydroxy($C_1$–$C_3$)alkyl, or halo($C_1$–$C_3$)alkyl;
$R^1$ is —$CH_2X$;

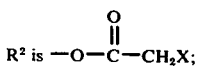

X is bromine, chlorine, fluorine, or iodine;
$R^3$ is hydrogen, $C_1$–$C_4$ alkyl, or $CF_3$;
$R^4$ is hydrogen, $C_1$–$C_4$ alkyl, $(CH_2)_nN(C_1$–$C_4$ alkyl$)_2$, $CH_2CH[O(C_1$–$C_4$ alkyl$)]_2$, $(CH_2)_n$-OH, 9-octadecenyl,

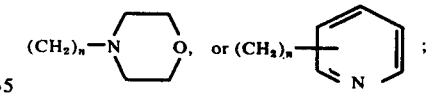

$R^5$ is NH or oxygen;
$R^6$ is $NH_2$, $NHCOCH_3$,

$R^7$ is hydrogen or —$CH_2CH_2SCH_3$;
n is 1, 2, 3, or 4;
and the nontoxic, pharmacologically-acceptable salts thereof.

2. The compound as in claim 1, said compound being 4-amino-1-methyl-3-(1-methyl-5-nitroimidazol-2-yl)-1H-pyrazolo-[3,4-d]pyrimidine hydrochloride.

3. The compound as in claim 1, said compound being 5-[2-(dimethylamino)ethyl]-4,5-dihydro-4-imino-1-methyl-3-(1-methyl-5-nitroimidazol-2-yl)-1H-pyrazolo[3,4-d]pyrimidine dihydrochloride.

4. The compound as in claim 1, said compound being 4,5-dihydro-4-imino-1-methyl-3-(1-methyl-5-nitroimidazol-2-yl)-5-propyl-1H-pyrazolo[3,4-d]pyrimidine.

5. The compound as in claim 1, said compound being 5-ethyl-4,5-dihydro-4-imino-1-methyl-3-(1-methyl-5-nitroimidazol-2-yl)-1H-pyrazolo[3,4-d]pyrimidine.

6. The compound as in claim 1, said compound being 1,5-dihydro-1,6-dimethyl-3-(1-methyl-5-nitroimidazol-2-yl)-4H-pyrazolo[3,4-d]pyrimidin-4-one.

7. The compound as in claim 1, said compound being 4,5-dihydro-4-imino-1-methyl-3-(1-methyl-5-nitroimidazol-2-yl)-5-propyl-1H-pyrazolo[3,4-d]pyrimidine mononitrate.

8. The compound as in claim 1, said compound being 4-hydrazino-1-methyl-3-(1-methyl-5-nitroimidazol-2-yl)-1H-pyrazolo[3,4-d]pyrimidine.

9. The compound as in claim 1, said compound being 4,5-dihydro-4-imino-1-methyl-3-(1-methyl-5-nitroimidazol-2yl)-5-(4-pyridylmethyl)-1H-pyrazolo[3,4-d]pyrimidine diphosphate.

10. The compound as in claim 1, said compound being 4,5-dihydro-4-imino-1-methyl-3-(1-methyl-5-nitroimidazol-2-yl)-5-(4-pyridylmethyl)-1H-pyrazolo[3,4-d]pyrimidine dinitrate.

11. The compound as in claim 1, said compound being 4-hydrazino-1-methyl-3-(1-methyl-5-nitroimidazol-2-yl)-1H-pyrazolo[3,4-d]pyrimidine monophosphate.

12. The compound as in claim 1, said compound being 4-hydrazino-1-methyl-3-(1-methyl-5-nitroimidazol-2-yl)-1H-pyrazolo[3,4-d]pyrimidine monosulfate.

13. The compound as in claim 1, said compound being 4,5-dihydro-4-imino-1-methyl-3-(1-methyl-5-nitroimidazol-2-yl)-5-(2-morpholinoethyl)-1H-pyrazolo[3,4-d]-pyrimidine diphosphate.

* * * * *

UNITED STATES PATENT AND TRADEMARK OFFICE
CERTIFICATE OF CORRECTION

PATENT NO. : 4,001,230

DATED : January 4, 1977

INVENTOR(S) : Henry Friedman

It is certified that error appears in the above-identified patent and that said Letters Patent are hereby corrected as shown below:

Column 1, line 27, which reads "Also in the prior art in" should read  Also in the prior art is  .

Column 2, line 15, structure should read

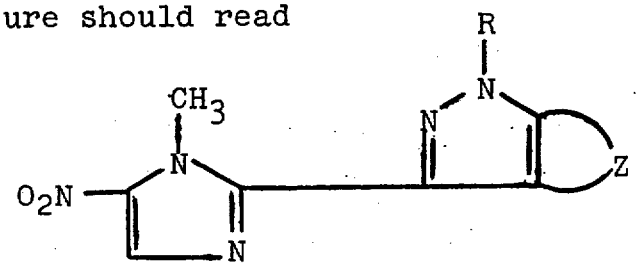

Column 2, line 34, "$R^2$ is" should be deleted.

Column 2, line 66, formula should read

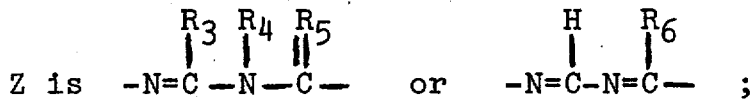

Column 4, line 6, "hyodrysenteriae" should read <u>hyodysenteriae</u>  .

Column 4, line 9, "methyl3" should read  methyl-3-  .

Column 4, line 13, should read  "where Z is"  .

Column 7, line 11, that portion of the formula which reads

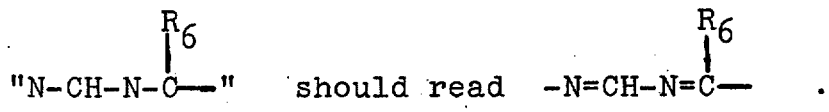

UNITED STATES PATENT OFFICE
CERTIFICATE OF CORRECTION

Patent No.  4,001,230   Dated January 4, 1977

Inventor(s) Henry Friedman

It is certified that error appears in the above-identified patent and that said Letters Patent are hereby corrected as shown below:

Column 13, line 26, which reads "amino-1-ethyl-(1-methyl-5-nitro-2-imidazolyl)-" should read amino-1-ethyl-3-(1-methyl-5-nitro-2-imidazolyl)- .

Column 21, Table 1, in Compound 1 with subhead "cattle", "1.56" should read $\leq 1.56$ .

Column 22, Table 1, in Compound 2 with heading "Vibrio coli" "1.56" should read $\leq 1.56$ .

Column 23, Table 1, in Compound 8n with subhead "cattle", "0.78" should read $\leq 0.78$ .

UNITED STATES PATENT OFFICE
CERTIFICATE OF CORRECTION

Patent No. 4,001,230  Dated January 4, 1977

Inventor(s) Henry Friedman  Page 3 of 3

It is certified that error appears in the above-identified patent and that said Letters Patent are hereby corrected as shown below:

Column 28, line 5, structure should read

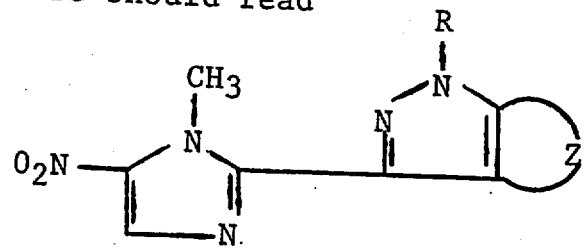

Column 28, line 41, should read

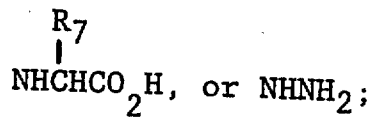

Signed and Sealed this

Tenth Day of May 1977

[SEAL]

Attest:

RUTH C. MASON
*Attesting Officer*

C. MARSHALL DANN
*Commissioner of Patents and Trademarks*